(12) United States Patent
Balch et al.

(10) Patent No.: US 12,252,724 B2
(45) Date of Patent: *Mar. 18, 2025

(54) BIOSYNTHESIS OF RETINOIDS

(71) Applicant: DSM IP ASSETS B.V., Heerlen (NL)

(72) Inventors: Nathalie Balch, Kaiseraugst (CH); Paul Blomquist, Kaiseraugst (CH); Reed Doten, Kaiseraugst (CH); Peter Houston, Kaiseraugst (CH); Ethan Lam, Kaiseraugst (CH); Jenna McMahon, Kaiseraugst (CH); Joshua Trueheart, Kaiseraugst (CH); Celine Viarouge, Kaiseraugst (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 18/161,236

(22) Filed: Jan. 30, 2023

(65) Prior Publication Data

US 2023/0227862 A1 Jul. 20, 2023

Related U.S. Application Data

(63) Continuation of application No. 16/647,730, filed as application No. PCT/EP2018/076033 on Sep. 25, 2018, now Pat. No. 11,578,344.

(60) Provisional application No. 62/562,712, filed on Sep. 25, 2017, provisional application No. 62/562,699, filed on Sep. 25, 2017, provisional application No. 62/562,672, filed on Sep. 25, 2017, provisional application No. 62/562,602, filed on Sep. 25, 2017.

(30) Foreign Application Priority Data

Apr. 20, 2018 (EP) .................................... 18168564
Jun. 5, 2018 (CH) .................................... 00715/18

(51) Int. Cl.
*C12P 7/22* (2006.01)
*C12N 9/04* (2006.01)
*C12N 9/10* (2006.01)
*C12P 7/62* (2022.01)

(52) U.S. Cl.
CPC .............. *C12P 7/22* (2013.01); *C12N 9/0006* (2013.01); *C12N 9/1029* (2013.01); *C12P 7/62* (2013.01); *C12Y 101/01105* (2013.01); *C12Y 203/0102* (2013.01)

(58) Field of Classification Search
CPC .... C12P 7/22; C12P 7/62; C12P 23/00; C12N 9/0006; C12N 9/1029; C12Y 101/01105; C12Y 203/0102; C12Y 203/01084; A61K 31/07
See application file for complete search history.

(56) References Cited

U.S. PATENT DOCUMENTS

| | | | |
|---|---|---|---|
| 7,851,199 B2 | 12/2010 | Bailey | |
| 8,691,555 B2 | 4/2014 | Bailey | |
| 9,644,217 B2 | 5/2017 | Kim | |
| 11,578,344 B2* | 2/2023 | Balch | ...................... C12P 23/00 |
| 11,905,542 B2* | 2/2024 | Balch | ................... C12N 9/1029 |
| 12,049,658 B2 | 7/2024 | Balch | |
| 2003/0166595 A1 | 9/2003 | Von Lintig | |
| 2004/0038209 A1 | 2/2004 | Von Lintig | |
| 2005/0059061 A1 | 3/2005 | Bachmann | |
| 2011/0039299 A1 | 2/2011 | Bailey | |
| 2014/0170720 A1 | 6/2014 | Kim et al. | |
| 2015/0322412 A1 | 11/2015 | Farrell | |
| 2016/0362709 A1 | 12/2016 | Kim | |
| 2020/0231993 A1 | 7/2020 | Balch | |
| 2020/0239924 A1 | 7/2020 | Balch | |
| 2020/0239925 A1* | 7/2020 | Balch | ...................... C12P 23/00 |
| 2020/0248151 A1 | 8/2020 | Balch | |
| 2020/0277644 A1* | 9/2020 | Balch | .............. C12Y 113/11063 |
| 2022/0064607 A1 | 3/2022 | Houston | |
| 2022/0356503 A1* | 11/2022 | Houston | ......... C12Y 113/11063 |
| 2023/0049760 A1 | 2/2023 | Mcmahon | |
| 2023/0407344 A1 | 12/2023 | Houston | |
| 2024/0018564 A1 | 1/2024 | Houston | |
| 2024/0279706 A1 | 8/2024 | Houston | |

FOREIGN PATENT DOCUMENTS

| | | |
|---|---|---|
| CN | 105339490 | 2/2016 |
| EP | 1031627 | 8/2000 |
| JP | 2016-501543 | 1/2016 |
| WO | 2008/042338 | 4/2008 |
| WO | 2009/009142 A2 | 1/2009 |
| WO | 2009/126890 A2 | 10/2009 |
| WO | 2014/096992 | 6/2014 |
| WO | 2022003130 | 1/2022 |
| WO | 2023006851 | 2/2023 |
| WO | 2023067030 | 4/2023 |
| WO | 2024160712 | 8/2024 |

OTHER PUBLICATIONS

International Search Report for PCT/EP2018/076033, mailed Nov. 22, 2018, 8 pages.
Written Opinion of the ISA for PCT/EP2018/076033, mailed Nov. 22, 2018, 10 pages.

(Continued)

*Primary Examiner* — Ganapathirama Raghu

(74) *Attorney, Agent, or Firm* — Nixon & Vanderhye P.C,

(57) ABSTRACT

The present invention is related to a novel enzymatic process for production of retinoids via a multi-step process, which process includes the use of heterologous enzymes having activity in a carotene-producing host cell, particularly wherein such process results in high percentage of retinoids, in trans-isoform.

20 Claims, No Drawings
Specification includes a Sequence Listing.

US 12,252,724 B2

Page 2

(56) References Cited

OTHER PUBLICATIONS

Bao-Jian Ding et al., "The Yeast ATF1 Acetyltransferase Efficiently Acetylates Insect Pheromone Alcohols: Implications for the Biological Production of Moth Pheromones", Lipids, vol. 51, No. 4, Jan. 22, 2016, pp. 469-475.

Hui-Jeong Jang, et al., "Retinoid production using metabolically engineered Escherichia coil with a two-phase culture system", Microbial Cell Factories 2011, 10:59, pp. 1-12.

Hui-Jeong Jang, et al., "Selective Retinol Production by Modulating the Composition of Retinoids From Metabolically Engineered E. coli", Biotechnology and Bioengineering, vol. 112, No. 8, Aug. 2015, 9 pages.

Alfonso Prado-Cabrero et al., "Retinal Biosynthesis in Fungi: Characterization of the Carotenoid Oxygenase CarX from Fusarium fujikuroi", Eukaryotic Cell, vol. 6, No. 4, Apr. 2007, pp. 650-657.

Unknown, Database UniProt, "SubName: Full=Oxidoreductase {ECO:0000313|EMBL:EXK27040.1}", XP002786088, 1 page, accessed on Oct. 25, 2018.

Unknown, Database UniProt, "SubName: Full=Alcohol acyl transferase {ECO:0000313|EMBL:AEM43830.1}" XP002786089, 1 page, accessed on Oct. 25, 2018.

Unknown, Database UniProt, "RecName: Full=Chloramphenicol acetyltransferase {ECO:0000256|RuleBase:RU000503}; EC=2.3.1.28 {ECO:0000256|RuleBase:RU000503}", XP002786090, 2 pages, accessed on Oct. 25, 2018.

Unknown, Database UniProt, "SubName: Full=1,2-diacyl-sn-glycerol:acetyl-CoA acetyltransferase {ECO:0000313|EMBL:ADF57327.1}", XP002786091, 1 page, accessed on Oct. 25, 2018.

Unknown, Database UniProt, "SubName: Full=Alcohol acyl transferase {ECO:0000313|EMBL:AAS79797.1}", XP002786092, 1 page, accessed on Oct. 25, 2018.

Unknown, Database UniProt, "SubName: Full=Coniferyl alcohol acyltransferase {ECO:0000313|EMBL:ABG75942.1}", XP002786093, 1 page, accessed on Oct. 26, 2018.

Unknown, Database UniProt, "SubName: Full=LAFE_OF18162g1_1 {ECO:0000313|EMBL:SCW02964.1}", XP002786094, 1 page, accessed on Oct. 26, 2018.

Unknown, Database UniProt, "SubName: Full=LAFE_0A06766g1_1 {ECO:0000313|EMBL:SCV99600.1}", XP002786095, 1 page, accessed on Oct. 26, 2018.

Unknown, Database UniProt, "SubName: Full=Putative carotenoid oxygenase {ECO:0000313|EMBL:CAH70723.1}", XP002786096, accessed on Dec. 17, 2018.

Unknown, Database UniProt, "RecName: Full=Zeaxanthin 7,8(7',8')-cleavage dioxygenase, chromoplastic; EC=1.13.11.84 {ECO:0000269|PubMed:12509521}; AltName: Full=CsZCD; AltName: Full=Zeaxanthin 7,8-dioxygenase; Flags: Precursor", XP002786097, 2 pages, accessed on Oct. 26, 2018.

Unknown, Database UniProt, "RecName: Full-Carotenoid isomerooxygenase; EC=1.13.11.65; AltName: Full=Beta-carotene 15,15'-monooxygenase and retinoid isomerase; AltName: Full-Beta-carotene dioxygenase and retinoid isomerase; AltName: Full= Neither inactivation nor afterpotential mutant B", XP002786098, mailed Dec. 17, 2018.

Unknown, Database UniProt, "Beta,beta-carotene 15,15'-dioxygenase [Esox lucius]", XP002786099, 2 pages, accessed on Oct. 26, 2018.

Hong et al., "Biochemical properties of retinoid-converting enzymes and biotechnological production of retinoids", Applied Microbiology and Biotechnology, vol. 99, No. 19, Aug. 1, 2015, pp. 7813-7826.

Estrada et al, "Ustilago maydis accumulates β-carotene at levels determined by a retinal-forming carotenoid oxygenase", Fungal Genetics and Biology, vol. 46, 2009, pp. 803-813.

Unknown, Database UniProt [Online], XP002786384, "Characterization of a gene in the car cluster of Fusarium fujikuroi that codes for a protein of the cartotenoid oxygenase family", Mar. 1, 2005, 1 page.

Unknown, Database UniProt [Online], XP002786385, "The complete DNA sequence of the mitochondrial genome of a 'living fossil,' the coelacanth (Latimeria chalumnae)", Apr. 18, 2012, 2 pages.

Unknown, Database UniProt [Online], XP002786386, "Filing the gap in vitamin A research. Molecular identification of an enzyme cleaving beta-cartotene to retinal," Oct. 16, 2013, 4 pages.

Unknown, Database UniProt [Online], XP002786387, Subname: Full-Zgc:63614 {ECO: 0000313 EMBL: AAH56789.1}, Jul. 5, 2004, 1 page.

Unknown, Database Protein [Online], XP002786388, "beta, beta-carotene 15.15'-dioxygenase-like [Ictalurus punctatus]", Jul. 6, 2016, 1 page.

Unknown, Database Protein [ONLINE], "beta, beta-carotene 15, 15'-dioxygenase [Esox Lucius]", Jan. 30, 2017, 1 page.

Seffernick et al., Melamine deaminase and Atrazine chlorohydrolase: 98 percent identical but functionally different. J. Bacterial., 2001, vol. 183 (8): 2405-2410. (Year: 2001).

Sen et al., Developments in directed evolution for enzyme functions. Appl. Biochem. Biotechnol., 2007, vol. 143: 212-223. (Year: 2007).

Whisstock et al., Prediction of protein function from protein sequence. Q. Rev. Biophysics., 2003, vol. 36 (3): 307-340. (Year: 2003).

Witkowski et al., Conversion of b-ketoacyl synthase to a Malonyl Decarboxylase by replacement of the active cysteine with glutamine. Biochemistry, 1999, vol. 38: 11643-11650. (Year: 1999).

Broun et al., Catalytic plasticity of fatty acid modification enzymes underlying chemical diversity of plant lipids. Science, 1998, vol. 282: 1315-1317. (Year: 1998).

Chen et al., Molecular mechanisms of the coordination between astaxanthin and fatty acid biosynthesis in Haematococcus pluvialis (Chlorophyceae). The Plant J., 2015, vol. 81: 95-107. (Year: 2015).

Chica et al., Semi-rational approaches to engineering enzyme activity: combining the benefits of directed evolution and rational design. Curr. Opi. Biotechnol., 2005, vol. 16: 378-384. (Year: 2005).

Devos et al., Practical limits of function prediction. Proteins: Structure, Function, and Genetics. 2000, vol. 41: 98-107. (Year: 2000).

Wikipedia, Acyl-CoA, 5 pages downloaded from https://en.wikipedia.org/wiki/Acyl-CoA on Jul. 23, 2021. (Year: 2021).

Enzyme-2.3.1.84 Alcohol 0-acetyltransferase, 2 pages downloaded from https://enzyme.expasy.org/ on Jul. 23, 2021 (Year: 2021).

Enzyme-2.3.1. 76 Retinal 0-fatty-acyltransferase, 2 pages https://enzyme.expasy.org/ on Jul. 23, 2021 (Year: 2021).

Menendez-Bravo et al., Metabolic engineering of microorganisms for the production of structurally diverse esters. Appl Microbial Biotechnol., 2017, vol. 101: 3043-3053. (Year: 2017).

Tang et al., Identification of Dehalobacter reductive dehydrogenases that catalyse dechlorination of chloroform, 1, 1, 1-trichloroethane and 1, 1-dichloroethane. Phil Trans R Soc B, 2013, vol. 368: 20120318, pp. 1-10. (Year: 2013).

Verstrepen et al., Expression Levels of the Yeast Alcohol Acetyltransferase Genes ATF1, Lg-ATF1, and ATF2 Control the Formation of a Broad Range of Volatile Esters. Appl Environ. Microbial., 2003, vol. 69(9): 5228-5237. (Year: 2003).

S. Thewes et al., "Characterization of a gene in the car cluster of Fusarium fujikuroi that codes for a protein of the carotenoid oxygenase family", published Jul. 28, 2005, Molecular Genetics and Genomics, vol. 274, pp. 217-228.

Database Protein, "Beta-carotene oxygenase 1, like [Esox lucius]", Jan. 30, 2017, retrieved from NCBI Database accession No. XP 010867139.2, 1 page.

Database Uniprot, "SubName: Full=Beta-carotene oxygenase 1 {ECO:0000313|Ensembl:ENSLACP00000000167}", H2ZRZ6, submitted Feb. 2012, 2 pages.

Database Uniprot, "SubName: Full=Zgc:63614 {ECO:0000313|EMBL:AAH56789.1}", Q6PGY1; submitted Aug. 2003, 1 page.

International Search Report for PCT/EP2018/076021 dated Dec. 6, 2018, 5 pages.

International Search Report for PCT/EP2018/076032 mailed Dec. 7, 2018, 7 pages.

(56) References Cited

OTHER PUBLICATIONS

International Search Report for PCT/EP2018/076034, mailed Nov. 13, 2018, 5 pages.
Written Opinion of the ISA for PCT/EP2018/076021 dated Dec. 6, 2018, 7 pages.
Written Opinion of the ISA for PCT/EP2018/076032 mailed Dec. 7, 2018, 9 pages.
Written Opinion of the ISA for PCT/EP2018/076034, mailed Nov. 13, 2018, 7 pages.
Akacha et al, "Microbial and enzymatic technologies used for the (I) CrMark production of natural aroma compounds: Synthesis, recovery modeling, and bioprocesses", Food and Bioproducts Processing, pp. 675-706 (2015).
Yen et al. "DGAT enzymes and triacylglycerol biosynthesis", Journal of Lipid Research, vol. 49, 2008, pp. 2283-2301.
Lintig et al; The Journal of Biological Chemistry, vol. 275, No. 16, pp. 11915-11920, Apr. 21, 2000.
O'Byrne, et al., "Retinol and retinyl esters: biochemistry and physiology: Thematic Review Series: Fat-Soluble Vitamins: Vitamin A", Journal of Lipid Research, vol. 54, No. 7, Jul. 1, 2013, pp. 1731-1743.
Ruiz et al., "Molecular and Biochemical Characterization of Lecithin Retinol Acyltransferase*" The Journal of Biological Chemistry, vol. 274, No. 6, 1999, pp. 3834-3841.
Schreiber et al., "Retinyl ester hydrolases and their roles in vitamin A homeostasis", Biochim Biophys Acta. 2012, pp. 113-123.
Sena "Substrate Specificity of Purified Recombinant Human B-Carotene 15, 15'-Oxygenase (BCO1)*" The Journal of Biological Chemistry, vol. 288 No. 52, 37094-37103 (2013) (Year: 2013).
U.S. Appl. No. 18/700,931, filed Apr. 12, 2024, Viyas et al., related application.

\* cited by examiner

SEQUENCE LISTING

```
Sequence total quantity: 43
SEQ ID NO: 1           moltype = AA  length = 787
FEATURE                Location/Qualifiers
source                 1..787
                       mol_type = protein
                       organism = Ustilago maydis
SEQUENCE: 1
MVKGSSNRRQ HSASLQGLPS SQHCAPVISI PSPPPPAEDH AYPPSSFTIP LSKDEELAEA   60
GPSRPGSSAI SRRPVLSRRR TSKKEYVHPY LSGNFAPVTT ECPLTDCLFE GTIPEEFAGS  120
```

```
QYVRNGGNPL ANSERDRDAH WFDADGMLAG VLFRRTPKGT IQPCFLNRFI LTDLLLSTPE   180
HSRLPYVPSI ATLVNPHTSV FWLLCEIIRT FVLAMLTWLP GLGLGGNQKL KRISVANTSV   240
FWHDGKAMAG CESGPPMRIM LPGLETAGWY TGEEDKEKET CDKNSGNSLT SSSSKGFGGG   300
PPIVSMLREF TTAHPKIDPR TQELLLYHMC FEPPYLRISV IPASQSKKTD LPAHAKTIKG   360
KAVRGLKQPK MMHDFGATAT QTVIIDVPLS LDMMNLVRGK PILHYDPSQP TRFGILPRYE   420
PERVRWYESA EACCIYHTAN SWDDDGKFDA SHEHATRSAI RGVNMLGCRL NSATLVYSAG   480
NLLPPSHVLP PPNCPEKCQL YYWRFDLEHA ETNTISHEFA LSDIPFEFPT INEDYSMQQA   540
CYVYGTSMRD GTFDAGLGKA AKIDALVKLD AQALIRKGKA MWSQGRLKAG DSVDTRTVEE   600
VLTAQRDGSA SPEDPIKIFE MPRGWYAQET TFVPRRSSTN ETSQEDDGWL VCYVFDEATG   660
LHPSTGEVLP GASSELWIID AKLMSRVVCR IKLPQRVPYG LHGTLFTEEQ IASQKPIDPS   720
QVRSWALSIN LADPFSSSAL GSTVYSAAGK AATSKFKNRE ETYAAFIKDP IRIGAWWVKR   780
NIELLIA                                                             787

SEQ ID NO: 2            moltype = DNA   length = 2364
FEATURE                 Location/Qualifiers
misc_feature            1..2364
                        note = Yarrowia codon-optimized UmCCO1
source                  1..2364
                        mol_type = other DNA
                        organism = synthetic construct
SEQUENCE: 2
atggttaagg gctcctctaa ccgacgacag cactccgctt cccttcaggg actcccttct    60
tctcagcact gtgcccccgt tatctctatt ccttctcccc ctcccctgc tgaggatcac   120
gcttacccc cttcctcttt cactattcct ctctccaagg atgaggagct tgctgaggcc   180
ggaccctctc gacccggttc ctctgctatt tctcgacgac ctgttctgtc tcgacgacga   240
acttctaaga aggagtacgt tcaccccgac ctctccggca acttgcccc tgttaccact   300
gagtgccctc tcaccgattg tctctttgag ggtactatcc ctgaggagtt tgctggctcc   360
cagtacgtcc gaaacggcgg aaaccccctt gccaactccg agcgagatcg agatgcccac   420
tggttcgatg ctgacggtat gctggctgga gttctctttc gacgaccccc aagggcacc   480
attcagcctt gtttcctcaa ccgattcatt ctcaccgacc tcctgctctc taccccctgg   540
cactctcgac tcccttacgt cccttccatc gctactctcg tcaacccca cacttccgtc   600
ttttggctcc tttgtgagat catccgaact ttcgttctgg ctatgcttac ctggctccct   660
ggcctcggac tcggtggcaa ccagaagctc aagcgaatct ctgttgctaa cacctccgtt   720
ttctggcacg acggaaaggc tatggctgga tgtgagtctg gacccctat gcgaatcatg   780
ctccctggtc ttgagactgc cggctggtac actgctgagg aggataagga gaaggagact   840
tgtgataaga actctggcaa ctctctcact tcttcctctt ctaagggttt tggcggaggc   900
cctcccattg tctccatgct tcgagagttt accactgctc accccaagat tgaccctcga   960
acccaggagc tccttctcta ccacatgtgc ttcgagcccc cttaccttcg aatctctgtc  1020
atccctgctt ctcagtctaa gaagactgac ctccctgctc acgctaagac cattaaggct  1080
aaggctgtgc gaggtcttaa gcagcccaag atgatgcacg atttcggcgc taccgccact  1140
cagaccgtca tcatcgacgt ccctctctcc ctcgacatga tgaacctcgt ccgaggcaag  1200
cccattctgc actacgatcc ctctcagcct acccgattcg gtattcttcc ccgatacgag  1260
cctgagcgag tgcgatggta cgagtctgcc gaggcttgct gtatctacca caccgccaac  1320
tcttgggatg acgatggcaa gtttgacgct tctcacgagc acgctaccg atccgccatc  1380
cgaggcgtca acatgctcgg ctgccgactc aactctgcca ccctcgtgta ctctgctgga  1440
aaccttctcc ctccctctca cgtccttccc cctcccaact gccctgagaa gtgtcagctc  1500
tactactggc gattcgacct tgagcacgct gagactaacc tcatttccca cgagtttgct  1560
ctgtccgaca ttcctttcga gttccccacc atcaacgagg actactctat gcagcaggct  1620
tgttacgttt acggtacttc catgcgagat ggcaccttg acgctggact cggaaaggct  1680
gctaagattg acgcccttgt taagctggac gctcaggccc ttattcgaaa gggcaaggcc  1740
atgtggtccc agggacgact taagctggaa gactctgtga cacccgaac cgttgaggag  1800
gttctcactg ctcagcgaga tggttctgcc tcccctgagg accctatcaa gattttcgag  1860
atgccccgag gatggtacgc tcaggagact accttcgtcc ctcgacgatc tctactaacg  1920
gagacttctc aggaggatga cggttggctc gtctgctacg tgttcgatga ggccactggc  1980
cttcaccctt ccaccggaga ggttctccct ggcgcttcct ccgagctgtg gatcattgat  2040
gccaagctca tgtcccgagt cgtttgccga atcaagctcc cccagcgagt ccccttacga  2100
ctccacggca ctctctttac cgaggagcag attgcctctc agaagcctat cgacccttct  2160
caggtccgat cctgggctct gtctatcaac cttgccgatc ccttctcctc ttccgccctt  2220
ggctctaccg tgtactccgc cgctggtaag gctgccacct ccaagtttaa gaaccgagag  2280
gagacttacg ctgccttcat caaggaccct atccgaatcg gcgcttggtg ggtcaagcga  2340
aacatcgagc tcctgattgc ttaa                                         2364

SEQ ID NO: 3            moltype = AA   length = 696
FEATURE                 Location/Qualifiers
source                  1..696
                        mol_type = protein
                        note = Fusarium fujikuroi
                        organism = unidentified
SEQUENCE: 3
MKFLQQNSFT QTSMSQPHED VSPAIRHPYL TGNFAPIHKT TNLTPCTYSG CIPPELTGGQ    60
YVRNGGNPVS HQDLGKDAHW FDGDGMLSGV AFRKASIDGK TIPEFVNQYI LTDLYLSRKT   120
TSIASPIMPS ITTLVNPLST MFQIMFATFR TIFLVILSNL PGSQQAIKRI SVANTAVLYH   180
DGRALATCES GPPMRIQLPS LDTVGWFDGV EAEGEPEISQ AGSDDSPFGG SGIFSFMKEW   240
TTGHPKVDPV TGEMLLYHNT FMPPYVHCSV LPKSNEKAPG HRLVNQPVLG VSGARMMHDF   300
GASRSHTIIM DLPLSLDPLN TMKGKEVVAY DPTKPSRFGV FPRHLPSSVR WFHTAPCCIF   360
HTANTWDSQS SEGELSVNLL ACRMTSSTLV YTAGNIRPPV RSRCTQARVW SDEREETACR   420
YKEAPALESP GESTGLADYF PITAESDDYD QCRLYYYEFD LAMESRNHVK SQWALSAIPF   480
EFPSVRPDRE MQEARYIYGC STSTSCFGVA LGRADKVDLL VKMDAKTLIQ RGKKMNATSI   540
TGCVDRRSVC EILQEQRKDD PIYIFRLPPN HYAQEPRFVP RACSTEEDDG YLLFYVFDES   600
```

```
QLLPSGDCPP SATSELWILD AKNMRDVVAK VRLPQRVPYG LHGTWFSSQD IESQRSVESL   660
RSLEVVQRKK EEWVNSGGQI RKSWMVLREK LEKAVG                            696

SEQ ID NO: 4            moltype = DNA  length = 2091
FEATURE                 Location/Qualifiers
misc_feature            1..2091
                        note = Yarrowia codon-optimized FfCarX
source                  1..2091
                        mol_type = other DNA
                        organism = synthetic construct
SEQUENCE: 4
atgaagtttc tccagcagaa ctcctttacc cagacctcta tgtctcagcc tcacgaggat    60
gtctctcccg ccattcgaca cccttacctt accggcaact ttgctcctat tcacaagacc   120
actaacctca ctccctgtac ttactctggc tgcattcccc ccgagcttac cggaggtcag   180
tacgttcgaa acggcggaaa ccctgtctcc caccaggatc tcggaaagga tgctcactgg   240
tcgatggcg acggtatgct ctcggcgtc gcctttcgaa aggcttccat tgatggcaag    300
actatccctg agttcgttaa ccagtacatt cttaccgacc tttaccttc tcgaaagacc   360
acctctattg cttcccctat tatgccctct atcaccaccc tggttaaccc tctctctact   420
atgtttcaga tcatgttcgc caccttccga actatcttcc tcgtcattct ctccaacctc   480
cctggttctc agcaggctat caagcgaatc tccgttgcca cactgctgt tctttaccac   540
gatggtcgag ctcttgccac ttgcgagtct ggccccccca tgcaatcca gcttccctcc   600
ctcgataccg ttggctggtt cgacgtgtt gaggctgagg gtgagcctga gatttctcag   660
gccggctctg atgactctcc cttcggcgg tccggcatct tctcctttat gaaggagtgg   720
accaccggcc accctaaggt ggaccccgtt accgagaga tgcttctcta ccacaacacc   780
ttcatgcctc cctacgtgca ctgctctgtt cttcccaagt ctaacgagaa ggctcccgga   840
caccgacttg ttaaccagcc cgttcttggt gtttctggtg cccgaatgat gcacgacttc   900
ggagcctctc gatctcacac tatcatcatg gaccttcccc tgtctctgga ccctctcaac   960
actatgaagg aaaggaggt tgttgcttac gaccctacca agccttctcg attcggtgtg  1020
ttcccccgac accttccctc ttccgtgcga tggtttcaca ctgctcttg ctgtatcttc  1080
cacactgcta acacttggga ttctcagtcc tctgagggag agctttctgt taacctcctt  1140
gcctgccgaa tgacctcttc taccttgtt tacactggtg gcaacatccg acctcccgtt  1200
cgatctcgat gtactcaggc ccgagtctgg tccgatgagc gagaggagac tgcttgtcga  1260
tacaaggagg ctcctgctct tgagtctcct ggtgagtcca ctggccttgc cgactacttt  1320
cccattaccg ctgagtccga cgactacgat cagtgccgac tctactacta cgagtttgac  1380
cttgctatgg agtcccgaaa ccacgtcaag tcccagtggg ctctctctgc cattcctttc  1440
gagtttccct ctgtgcgacc tgaccgagag atgcaggagg ctcgatacat ctacggctgt  1500
tccacttcca cttcttgctt cggtgtggct ctcggacgag ctgataaggt tgaccttctc  1560
gttaagatgg atgccaagac cctcattcag cgaggaaaga agataaacgc tacttccatc  1620
accggatgcg ttgatcgacg atctgtctgc gagatccttc aggagcagcg aaaggatgac  1680
cctatttaca ttttccgact tccccctaac cactacgctc aggagccccg attcgttccc  1740
cgagcttgtt ctactgagga ggacgacgga tacctccttt ctacgtgtt cgacgagtct  1800
cagtcccttc cctctggcga ttgtcctccc tctgctactt ctgagctttg gattcttgac  1860
gctaagaaca tgcgagatgt tgtggccaag gtccgacttc cccagcagtt tccttacggt  1920
ctgcacggta cttggttctc ttctcaggat attgagtctc agcgatctgt ggagtctctt  1980
cgatctcttg aggttgtgca gcgaaagaag gaggagtggg ttaactctgg aggccagatt  2040
cgaaagtcct ggatggttct tcgagagaag ctggagaagg ctgttggata g           2091

SEQ ID NO: 5            moltype = AA  length = 369
FEATURE                 Location/Qualifiers
source                  1..369
                        mol_type = protein
                        organism = Crocus sativus
SEQUENCE: 5
MQVDPTKGIG LANTSLQFSN GRLHALCEYD LPYVVRLSPE DGDISTVGRI ENNVSTKSTT    60
AHPKTDPVTG ETFSFSYGPI QPYVTYSRYD CDGKKSGPDI PIFSFKEPSF VHDFAITEHY   120
AVFPDIQIVM KPAEIVRGRR MIGPDLEKVP RLGLLPRYAT SDSEMRWFDV PGFNMVHVVN   180
AWEEEGGEVV VIVAPNVSPI ENAIDRFDLL HVSVEMARIE LKSGSVSRTL LSAENLDFGV   240
IHRGYSGRKS RYAYLGVGDP MPKIRGVVKV DFELAGRGEC VVARREFGVG CFGGEPFFVP   300
ASSKKSGGEE DDGYVSYLH DEGKGESSFV VMDARSPELE ILAEVVLPRR VPYGFHGLFV    360
TEAELLSQQ                                                          369

SEQ ID NO: 6            moltype = DNA  length = 1110
FEATURE                 Location/Qualifiers
misc_feature            1..1110
                        note = Yarrowia codon-optimized CsZCO
source                  1..1110
                        mol_type = other DNA
                        organism = synthetic construct
SEQUENCE: 6
atgcaggtgg accccaccaa gggtatcggc ctggccaaca cttctctcca gttctccaac    60
ggacgactcc acgctctttg cgagtacgac ctcccctacg tcgttcgact ctcccccgag   120
gacggtgaca tctctaccgt cggacgaatc gagaacaacg tttctactaa gtctaccacc   180
gcccacccca agaccgaccc cgtcaccgga gagaccttct ctttctccta cggtcccatt   240
cagccctacg tcacctactc ccgatacgac tgcgacggca agaagtccgg ccccgacttg   300
cccatcttct cttttcaagga gcccctcttt gtccacgact tcgccatcac cgagcactac   360
gccgtctttc ccgacattca gatcgtgatg aagcccgccg agatcgttcg aggacgacga   420
atgatcggcc ccgaccttga gaaggtcccc gactgggcc ttctcccccg atacgccacc   480
tccgactccg agatgcgatg gttcgacgtg cccggtttca acatggttca cgtggttaac   540
gcttgggag aggaggcgg agaggtcgtg gtcatcgtgg ccccccaacgt gtcccccatt   600
```

```
gagaacgcca tcgaccgatt cgacctcctc cacgtgtctg tggagatggc ccgaatcgag    660
ctgaagtccg gttccgtgtc ccgaacccct ctctctgccg agaacctcga tttcggtgtg    720
attcaccgag gctactccgg tcgaaagtcc cgatacgctt acctcggagt cggcgacccc    780
atgcccaaga ttcgaggtgt ggtcaaggtg gacttcgagc tggccggacg aggagagtgc    840
gtggttgccc gacgagagtt cggcgtgggt tgtttcgtg gagagcccct ctttgtcccc     900
gcttcttcca agaagtctgg aggcgaggag gacgatggc acgttgtgtc ttaccttcac     960
gacgagggaa agggagagtc ctctttcgtc gtgatgaacc tcgatctcc cgagctggag    1020
attcttgccg aggtggttct gccccgacga gttccctacg gttttcacgg cctctttgtt   1080
accgaggccg agcttctctc ccagcagtag                                    1110

SEQ ID NO: 7              moltype = AA  length = 620
FEATURE                   Location/Qualifiers
source                    1..620
                          mol_type = protein
                          organism = Drosophila melanogaster
SEQUENCE: 7
MAAGVFKSFM RDFFAVKYDE QRNDPQAERL DGNGRLYPNC SSDVWLRSCE REIVDPIEGH    60
HSGHIPKWIC GSLLRNGPGS WKVGDMTFGH LFDCSALLHR FAIRNGRVTY QNRFVDTETL   120
RKNRSAQRIV VTEFGTAAVP DPCHSIFDRF AAIFRPDSGT DNSMISIYPF GDQYYTFTET   180
PPFMHRINPCT LATEARICTT DFVGVVNHTS HPHVLPSGTV YNLGTTMTRS GPAYTILSFP   240
HGEQMFEDAH VVATLPCRWK LHPGYMHTFG LTDHYFVIVE QPLSVSLTEY IKAQLGGQNL   300
SACLKWFEDR PTLFHLIDRV SGKLVQTYES EAFFYLHIIN CFERDGHVVV DICSYRNPEM   360
INCMYLEAIA NMQTNPNYAT LFRGRPLRFV LPLGTIPPAS IAKRGLVKSF SLAGLSAPQV   420
SRTMKHSVSQ YADITYMPTN GKQATAGEES PKRDAKRGRY EEENLVNLVT MEGSQAEAFQ   480
GTNGIQLRPE MLCDWGCETP RIYYERYMGK NRYFYAISS DVDAVNPGTL IKVDVWNKSC    540
LTWCEENVYP SEPIFVPSPD PKSEDDGVIL ASMVLGGLND RYVGLIVLCA KTMTELGRCD   600
FHTNGPVPKC LHGWFAPNAI                                              620

SEQ ID NO: 8              moltype = DNA  length = 1863
FEATURE                   Location/Qualifiers
misc_feature              1..1863
                          note = Yarrowia codon-optimized DmNinaB
source                    1..1863
                          mol_type = other DNA
                          organism = synthetic construct
SEQUENCE: 8
atggccgctg gtgttttcaa gtcttttatg cgagatttct tgctgttaa gtacgatgag     60
cagcgaaacg accccaggc cgagcgactg acggcaacg gacgactgta cccaactgc     120
tcctctgatg tttggcttcg atcttgcgag cgagagatcg ttgaccccat tgagggccac   180
cactccggtc acattcccaa gtggatttgc ggttccctgc tccgaaacgg ccccggctct   240
tggaaggttg gcgacatgac cttcggccac ctgttcgact gctccgccct gctccaccga   300
tttgccattc gaaacggacg agtcacctac cagaaccgat tgttgacac tgagactctg   360
cgaaagaacc gatctgccca gcgaattgtt gtcaccgagt ttggcactgc cgctgttccc   420
gatccctgtc actccatctt cgaccgattt gccgccattt tcgaccga ttctggaacc    480
gataactcca tgatttccat ctaccccttc ggcgaccagt actacactt caccgagact   540
ccctttatgc accgaattaa ccctgcact ctcgctactg aggctcgaat ctgcaccacc    600
gacttcgttg gcgttgtcaa ccacacttct caccccacg ttcttccctc tggcactgtt    660
tacaacctgg gcaccactat gacccgatct ggaccgcgtt acactatcct ctcttttccc   720
cacggcgagc agatgttcga ggacgctcac gttgtcgcca ctctgccctg ccgatggaag   780
ctgcaccccg gttatatgca caccttcggc ctcactgacc actactttgt cattgttgag   840
cagccccttt ccgttccct cactgagtac atcaaggcc agcttggcgg acagaaccct     900
tccgcttgcc tcaagtggtt cgaggaccga cccactctct ttcaccttat tgatcgagtt   960
tccggcaagc tggtccagac ctacgagtcc gaggcttct tctacctgca catcatcaac   1020
tgctttgagc gagatggcca cgttgtcgtt gacatttgct cttaccgaaa ccccgagatg   1080
attaactgca tgtacctgga ggccattgcc aatgcagaa ctaaccccaa ctacgctacc   1140
ctctttcgag gacgacccct tcgattcgtc ctgcccctcg gcactattcc ccccgcctct   1200
atcgccaagc gaggactcgt caagtccttc tccctcgctg gactccgc tccccaggtt    1260
tctcgaacca tgaagcactc cgtttctcag tacgccgata ttacctacat gcccaccaac   1320
ggaaagcagg ccactgctgg agagagtcc cccaagcgag atgccaagcg aggccgatac   1380
gaggaggaga accttgtcaa cctggttact atggagggct ctcaggccga ggcttttcag   1440
ggcaccaacg gcattcagct tcgacccgag atgctgtgtg attggggctg tgagactccc   1500
cgaatctact acgagcgata catgggcaag aactaccgat acttctacgc catttcttcc   1560
gatgttgatg ctgtcaaccc cggcaccctc atcaaggttg atgtctggaa caagtcttgt   1620
cttacctggt gcgaggagaa cgttcacccc tctgagccca ttttcgtccc ctctcccgat   1680
cccaagtccg aggacgatgg cgttatcctg gcctctatgg ttcttggcgg tcttaacgac   1740
cgatacgtcg gccttattgt tctcttgtgcc aagaccatga ccgagctggg ccgatgtgat   1800
ttccacacca acggacccgt tcccaagtgc ctccacggtt ggtttgctcc caacgccatt   1860
tag                                                                1863

SEQ ID NO: 9              moltype = AA  length = 525
FEATURE                   Location/Qualifiers
source                    1..525
                          mol_type = protein
                          organism = Danio rerio
SEQUENCE: 9
MLSFFWRNGI ETPEPLKADV SGSIPPWLQG TLLRNGPGLF SVGNTSYKHW FDGMALIHSF    60
TFKDGEVFYR SKYLKSETYK KNIAADRIVV SEFGTMVYPD PCKNIFSRAF SYMMNAIPDF   120
TDNNLINIIK YGEDYYASSE VNYINQIDPL TLETLGRTNY RNHIAINLAT AHPHYDEEGN   180
TYNMGTAIMN LGRPKYVIFK VPANTSDKEN KKPALSEVEQ VCSIPRPSL YPSYFHSFGM    240
```

```
TENYIIFVEQ AFKLDIVKLA TAYFRDINWG SCLKFDQDDI NVFHLVNKKT GKAVSVKYYT    300
DPFVTFHHIN AYEDDGHVVF DLITYKDSKL YDMFYIQNMK QDVKRFIETN KDFAQPVCQR    360
FVLPVNVDKE TPQDINLVKL QDTTATAVLK EDGSVYCTPD IIFKGLELPA INYKFNSKKN    420
RYFYGTRVEW SPYPNKVAKV DVVTRTHKIW TEEECYPSEP VFIASPDAVD EDDGVILSSV    480
VSFNPQRPPF LVVLDAKSFK EIARATIDAS IHMDLHGLFI HDKST                    525

SEQ ID NO: 10            moltype = DNA   length = 1578
FEATURE                  Location/Qualifiers
misc_feature             1..1578
                         note = Yarrowia codon-optimized DrBCO
source                   1..1578
                         mol_type = other DNA
                         organism = synthetic construct
SEQUENCE: 10
atgctctctt tcttctggcg aaacggtatc gagacccccg agcccctcaa ggctgacgtt      60
tccggctcta tccctccctg gcttcaggga acccttctcc gaaacggtcc tggtctgttc     120
tccgttggca cacttcctca aagcactgg ttcgatggta tggctctcat tcactccttc      180
acctttaagg atggtgaggt tttttaccga tcaagtacga tcaagtctga gacttacaag     240
aagaacatcg ctgccgaccg aatcgttgtg tctgagttcg aaccatggt gtaccccgat      300
ccctgcaaga acatttctc ccgagccttc tcttacatga tgaacgccat tcctgacttt      360
accgataaca acctcattaa catcattaag tacggtgagg attactacgc ctcctctgag     420
gtcaactaca tcaaccagat tgacccctg acccttgaca tctcggacga aactaactac      480
cgaaaccaca ttgccatcaa ccttgccact gctcaccctc actacgacga ggagggtaac     540
acttacaaca tgggcactgc tattatgaac ctcggtcgac ccaagtacgt gattttcaag     600
gtgccgcca cacctctga taaggagaac aagaagcctg ccctctctga ggtggagcag       660
gtttgctca ttcccatccg accctcccct tacccttcct acttccactc ttttggcatt      720
actgagaact acatcatctt cgttgagcag gccttcaagc tggacatcgt caagctggct    780
actgcttact tccgagatat taactgggga tcttgcctta agttcgacca ggatgacatt    840
aacgtgttcc acctggtcaa caagaagact ggtaaggctg tgtccgtgaa gtactacact    900
gacccctttg ttaccttcca ccacatcaac gcttacgagg acgatggcca cgtcgtcttc    960
gatctcatta cttacaagga ctctaagctg tacgatatgt tctacattca gaacatgaag   1020
caggacgtca agcgatttat tgagactaac aaggacttcg ctcagccgt gtgccagcga    1080
tttgtccttc ccgtcaacgt tgataaggag acccctcagg acatcaacct tgtcaagctg   1140
caggacacca ctgccactgc tgtcctgaag gaggacggct ctgtctactg caccccttga   1200
atcattttta agggtcttga gctccctgct atcaactaca agttaactc taagaagaac   1260
cgatacttct acggcacccg agtggagtgg tccccttacc ctaacaaggt cgctaaggtg   1320
gacgttgtta ctcgaaccca caagatttgg actgaggagg agtgttaccc ttctgagcct   1380
gtctttattg cctcccctga cgccgttgat gaggatgacg gtgtgattct ttcttctgtg   1440
gtttctttca acccccagcg acccccttttc ctggttgtcc tcgatgctaa gtccttcaag   1500
gagattgctc gagctaccat cgatgcctct attcacatgg accttcacgg ccttttcatc   1560
cacgacaagt ctacctaa                                                  1578

SEQ ID NO: 11            moltype = AA   length = 281
FEATURE                  Location/Qualifiers
REGION                   1..281
                         note = Danio rerio BCO TPI aa
source                   1..281
                         mol_type = protein
                         organism = synthetic construct
SEQUENCE: 11
KQKSNHILQY SPVITASITP VQVSLGFLFT DTVIYLTISL QVTQKVHVGN EPQTKTRYDK     60
IALFDAEFDG VSIGVMTFIC IHTKKSWWYF CVITSDIYAP PNPPATVKSV SLLYMLTKPP    120
TVQRNPSAKS HNQLITTHPM TSPQILYAFR HYYSSLQRRC LRFHFCSITS LNPYRQIRPW    180
HVSRLISPRV LHQGGGVRNT VRAHSKGVRV RASDNIAWTR RHILDFWARC IHLLRFPTLP    240
PVSPSQPIEG NLIRDTFVIH SQIYKQCHSP SYSYIQHNYI Q                        281

SEQ ID NO: 12            moltype = DNA   length = 880
FEATURE                  Location/Qualifiers
misc_feature             1..880
                         note = Yarrowia codon-optimized DrBCO-TPI
source                   1..880
                         mol_type = other DNA
                         organism = synthetic construct
SEQUENCE: 12
aaacaaaaga gctgaaatca tatccttcag tagtagtata gtcctgttat cacagcatca      60
attaccccg tccaagtaag ttgattggga tttttgttta cagatacagt aatatacttg     120
actatttctt tacaggtgac tcagaaagtg catgttggaa atgagccaca gaccaagaca    180
agatatgaca aaattgcact attcgatgca gaattcgacg gtgtttccat tggtgttatg    240
acattcatct gcattcatac aaaaaagtct tggtagtggt actttgcgt tattacctcc    300
gatatctacg caccccccaa ccccccctgct acagtaaaga gtgtgagtct actgtacatg    360
cttactaaac cacctactgt acagcgaaac ccctcagcaa aatcacacaa tcagctcatt    420
acaacacacc caatgacctc accacaaatt ctatacgcct tttgacgcca ttattacagt    480
agcttgcaac gccgttgtct taggttccat ttttagtgct ctattcctc acttaacccg    540
tagaagtaac tcaggccatg gcactaagtg tagagctagg gttgatatc gccacgagtg    600
ctccatcagg gctagggtgg ggttagaaat acagtccgtg cgcactcaaa aggcgtccgg    660
gttagggcat ccgataatat cgcctggact cggcgccata ttctgacttt ctgggcgcgt    720
tgtattcatc tcctccgctt cccaacactt ccacccgttt ctccatccca accaatagaa    780
tagggtaacc ttattcggga cactttcgtc atacatagtc agatatacaa gcaatgtcac    840
tctccttcgt actcgtacat acaacacaac tacattcaaa                         880
```

```
SEQ ID NO: 13               moltype = AA   length = 531
FEATURE                     Location/Qualifiers
source                      1..531
                            mol_type = protein
                            organism = Ictalurus punctatus
SEQUENCE: 13
MEAIFCRNGT ETPEPVKAVV SGAIPPWLQG TLLRNGPGLF SIGKTSYNHW FDGLSLIHSF    60
TFKHGDVYYR SKFLRSDTYK KNIAANRIVV SEFGTMVYPD PCKNIFSKAF TYLLNSIPDF   120
TDNNLVSIIK YGDDYYTSSE INYINQINPV TLDTIGRANY RNYISLNLAT AHPHYDDEGN   180
TYNMGTAILA MSGPKYVIFK VPATTSDIKD NGKTNLALKN LQQICAIPFR SKLYPSYYHS   240
FGMTQNYIIF VEQPFKLDII RLATAYFRRT TWGKCLFYDQ DDVTLFHIIN RKTGDAVNTK   300
FYGDALVVFH HINAYEEDGH IVFDLISYKD SSLYDLFYID YMKQEAPKFT ETSKAFSRPV   360
CQRFVIPLNA DLKGNPLGKN LVRLEDTSAT AVFQMDGSLY CTPETLFQGL ELPSINYQYN   420
GKKYRYFYGS MMDWSPQANK IAKVDVDTKT HLEWTEEDCY PSEPKFVASP GAVDEDNGVI   480
LSSVVSVNPK KSPFMLVLDA KTLKEIARAS IDATVHLDLH GIFIPQETEL K            531

SEQ ID NO: 14               moltype = DNA   length = 1596
FEATURE                     Location/Qualifiers
misc_feature                1..1596
                            note = Yarrowia codon-optimized IpBCO
source                      1..1596
                            mol_type = other DNA
                            organism = synthetic construct
SEQUENCE: 14
atggaggcca tttttctgtcg aaacggcacc gagactcccg agcccgtcaa ggctgttgtg    60
tccggtgcta tccccccttg gcttcaggga acccttctcc gaaacggacc cggccttttc   120
tccattggta agacttccta caaccactgg tttgacggac tctctcttat tcactctttc   180
acctttaagc acggtgatgt ttactaccga tctaagttcc tccgatccga tacctacaag   240
aagaacattg ctgccaaccg aatcgttgtg tctgagtttg gcactatggt ctaccccgat   300
ccctgcaaga acattttctc taaggccttc acttacctgc tcaactctat tcccgatttc   360
accgacaaca accttgtctc tattattaag tacggcgatg actactacac ttcttccgag   420
attaactaca tcaaccagat caaccccgtt actctcgaca ctattggacg agccaactac   480
cgaaactaca tttcccttaa ccttgctact gcccaccctc actacgatga cgagggaaac   540
acctacaaca tgggcactgc tatcctggct atgtctggac ccaagtacgt catcttcaag   600
gtgcccgcta ctacctctga tattaaggac aacggaaaga ctaaccttgc tctgaagaac   660
ctgcagcaga tctgcgccat tccttttcga tctaagctct accttctta ctaccactcc    720
tttggtatga ctcagaacta catcattttc gttgagcagc ccttcaagct ggacattatt   780
cgactggcca ctgcttactt ccgacgaacc acctgggga agtgcctctt ttacgaccag   840
gacgatgtta ctctccttcca cattatcaac cgaaagactg gtgacgccgt gaacactaag   900
ttctacggtg atgctctcgt ggttttccac cacatcaacg cctacgagga ggacggccac   960
atcgttttg acctgatctc ttacaaggac tcttctctct acgaccttt ctacattgac   1020
tacatgaagc aggaggctcc taagttcact gagacttcca aggcttttc tcgacccgtt   1080
tgtcagcgat tcgtcatccc tctcaacgct gacctcaagg gaaacccct gggcaagaac   1140
cttgtccgac ttgaggacac ttctgctacc gctgtgttcc agatggacgg ttccctgtac   1200
tgtactcccg agactctctt tcagggtctt gagctccctt ccattaacta ccagtacaac   1260
ggaaagaagt accgatactt ctacggctct atgatggatt ggtcccctca ggctaacaag   1320
atcgctaagg tggacgttga taccaagact caccttgagt ggaccgagga ggattgctac   1380
ccttctgagc ctaagtttgt cgcttcccct ggcgctgtcg atgaggataa cggtgtgatc   1440
ctgtcttctg ttgtctccgt caaccccaag aagtcccct ttatgctcgt gctcgatgct   1500
aagaccctca aggagatcgc tcgagcctct attgacgcca ctgttcacct cgacctccac   1560
ggaattttca tccctcagga gactgagctt aagtaa                              1596

SEQ ID NO: 15               moltype = AA   length = 527
FEATURE                     Location/Qualifiers
source                      1..527
                            mol_type = protein
                            organism = Esox lucius
SEQUENCE: 15
MAQIIFGKNG TESPEPVKAE ITGCIPEWLQ GTLLRNGPGL FKVGDTEYNH WFDGMALIHS    60
FTFKDGVYY RSKFLRSDTF QKNTKANKIV VSEFGTMIYP DPCKNMFSKA FSYLLAAIPD   120
FTDNNLINII RYGEDYYASS EINYINQIDP VTLEVIGKMN YRKHISLNLA TAHPHYDEEG   180
NTYNMGIALM RFGMPKYVIF KVPVDASDKE GKKPALEEVE QVCNIPFRST LFPSYFHSFG   240
MSENYIIFVE QPFKDILRL ATANFRGSTW GSCLKYDED ITLIHLVDKK TGKAVSTKFY   300
ADALVVFHHI NAYEDDNHVV FDMITYKDSN LYEMFYLANM REESNKFIED KVNFSQPICQ   360
RFVLPLNVDK DTTKGTNMVM LKNTTAKAVM QDDGSVYCKP DTIFAGLELP GINYKFNGKK   420
YRYFYGSRVE WTPFPNKIGK VDILTKKHIE WTEEECYPSE PVFVASPGAM EEDDGVILSS   480
IVSLNPNKSP FMLVLNAKNF EEIARASIDA SVHLDLHGLF IPSQKTN                 527

SEQ ID NO: 16               moltype = DNA   length = 1584
FEATURE                     Location/Qualifiers
misc_feature                1..1584
                            note = Yarrowia codon-optimized ElBCO
source                      1..1584
                            mol_type = other DNA
                            organism = synthetic construct
SEQUENCE: 16
atggctcaga ttatttttgg caagaacggc actgagtctc ctgagcctgt caaggccgag    60
attaccggat gtatccctga gtggctccag ggtactctcc tccgaaacgg tcccggtctt   120
```

```
ttcaaggtgg gtgataccga gtacaaccac tggttcgatg gcatggccct gattcactct  180
tttaccttca aggatggtga cgtgtactac cgatctaagt tccttcgatc cgacaccttc  240
cagaagaaca ctaaggctaa caagattgtt gtgtctgagt ttggcaccat gatttaccct  300
gaccctgca agaacatgtt ttccaaggct ttctcctacc tccttgctgc catccctgac  360
ttcaccgata caacctgat taacattatc cgatacggtt aggactacta cgcctcttcc  420
gagatcaact acatcaacca gattgaccct gttaccctgg aggtgattgg aaagatgaac  480
taccgaaagc acatttctct gaaccttgct actgcccacc tcactacga cgaggaggga  540
aacacttaca acatgggaat cgccctcatg cgatttggca tgcccaagta cgtcatcttc  600
aaggttcctg tcgatgcttc tgataaggag ggcaagaagc ctgcccttga ggaggtggaa  660
caggtctgca acattccctt tcgatctacc ctcttccct cttacttcca ctctttggc  720
atgtctgaga actacatcat ctttgtcgag cagcctttca agctggacat cctccgactg  780
gccactgcta acttccgagg atctacctgg ggttcctgcc tgaagtacga caaggaggac  840
attactctca tccacctggt cgacaagaag actggtaagg ctgtttccac caagttctac  900
gctgatgctc tggttgtttt ccaccacatt aacgcctacg aggacgacaa ccacgtggtt  960
ttcgatatga tcacctacaa ggactccaac ctgtacgaga tgttctacct tgctaacatg  1020
cgagaggagt ctaacaagtt cattgaggac aaggtcaact tctcccagcc tatctgccag  1080
cgatttgtcc tccccctcaa cgttgacaag ataccacta agggaaccaa catggtgatg  1140
ctcaagaaca ctaccgccaa ggccgtgatg caggatgagc gctctgtgta ctgcaagcct  1200
gacaccattt ttgctggtct tgagctcccc ggcattaact acaagttcaa cggcaagaag  1260
taccgatact tttacggctc tcgagtggga tggactccct tccctaacaa gattggaaag  1320
gtggacattc tgaccaagaa gcacattgag tggaccgagg aggagtgtta ccctctgag  1380
ccgttttttg ttgcctcccc cggagctatg gaggaggata ggagtcat ctttctctc  1440
attgtctctc tcaaccctaa caagtccccc ttcatgcttg tcctcaacgc taagaactt  1500
gaggagattg ctcgagcctc catcgatgcc tctgttcacc tcgatctcca cggactcttc  1560
attccctctc agaagactaa ctag                                         1584

SEQ ID NO: 17           moltype = AA   length = 531
FEATURE                 Location/Qualifiers
source                  1..531
                        mol_type = protein
                        organism = Latimeria chalumnae
SEQUENCE: 17
MQSLFGKNKR ECPEPIKAEV KGQIPAWLQG TLLRNGPGMH TVGETSYNHW FDGLALMHSF   60
TFKDGEVFYQ SKYLRSDTYK KNMEANRIVV SEFGTMAYPD PCKNIFSKAF SYLSHTIPEF  120
TDNCLINIMK CGEDYYAVTE TNFIRKIDPK SLDTLEKVDY TKYIALNLAS SHPHYDAAGD  180
TINMGTSIAD KGKTKYLIVK IPNMKPVESE KKKKVYFKNL EVLCSIPSHG RLNPSYYHSF  240
GITENYIVFV EQPFKLDLLK LATAYFRGIN WASCLNFHSE DKTFIHIIDR RTKTSVSTKF  300
HTDALVLYHH VNAYEEDGHV VFDVIAYNDS SLYDMFYLAN VRQESAEFEA KNTSSSKPAC  360
RRFVIPLQPD KDAELGTNLV KLASTTADAI KEKDSIYCHP EILVEDIELP RINYNYNGKK  420
YRYIYVTGIA WKPIPTKIVK FDTLTRKSVE WQEEDCWPAE PVFVPSPDAK EEDDGIVLSS  480
IVCTSPNKFP FLLILDAKTF TELARASINA DVHLDLHGYF IPEKKKAQIT H          531

SEQ ID NO: 18           moltype = DNA   length = 1596
FEATURE                 Location/Qualifiers
misc_feature            1..1596
                        note = Yarrowia codon-optimized LcBCO
source                  1..1596
                        mol_type = other DNA
                        organism = synthetic construct
SEQUENCE: 18
atgcagtctc tgttcggtaa gaacaagcga gagtgtcctg agcccattaa ggctgaggtg   60
aagggtcaga ttcctgcttg gctccagggt actctcctcc gaaacggccc tggcatgcac  120
accgttggcg agacttctta caaccactgg ttcgacggac tcgctcttat gcactccttc  180
acctttaagg atggtgaggt ttttaccag tctaagtacc tgcgatccga cacctacaag  240
aagaacatgg aggccaaccg aattgtcgtg tctgagttcg gaaccatggc ctaccccgat  300
ccctgcaaga acatttttc caaggctttt tcttaccttt ctcacaccat ccctgagttt  360
accgacaact gtctgatcaa cattatgaag tgtggtgagg attactacgc tgttactgag  420
actaacttca tccgaaagat tgatcccaag tccctcgaca ccctggagaa ggttgactac  480
accaagtaca ttgctcttaa cctggcttcc tcccacccc actacgatgc tgctggtgat  540
accattaaca tgggcaccTc tatcgctgat aagggaaaga ctaagtacct gattgttaag  600
attcccaaca tgaagcccgt tgagtctgag aagaagaaga aggtctactt taagaacctg  660
gaggtgctct gctccatccc ttctcacgga cgacttaacc cttcttacta ccactccttt  720
ggcatcactg agaactacat cgttttcgtg gagcagccct ttaagctgga ccttctcaag  780
ctggccaccg cctacttccg aggtattaac tgggcctcct gtcttaactt ccactccgag  840
gacaagactt tcattcacat catcgatcga cgaaccaaga cctccgtttc cactaagttt  900
cacaccgatg ctctcgttct ttaccaccac gtcaacgctt acgaggagga tggccacgtt  960
gttttcgatg tcattgccta caacgactct tctctctacg atatgtttta cctgccaac  1020
gttgacagg agtctgccga gtttgaggct aagaacacct tcctccaga gctgcttgt  1080
cgacgatttg tcattcccct gcagcctgac aaggatgctg agctgggcac taacctggtc  1140
aagctcgctt ccactaccgc cgacgccatt aaggagaagg actccattta ctgccaccct  1200
gagatcctgg ttgaggatat tgagctccct cgaattaact acaactacaa cggcaagaag  1260
taccgataca tttacgttac tggtatcgcc tggaagccca ttcccactaa gattgtcaag  1320
tttgacactc tcactcgaaa gtccgtggag tggcaggagg aggactgttg gccgccgag  1380
cctgtcttcg ttccttcccc cgatgccaag gaggaggatg atggtattgt tcttcttcc  1440
atcgtgtgta cttcccctaa caagtttccc ttcctcctta ttctggacgc caagaccttt  1500
accgagctcg ctcgagcttc tattaacgcc gatgtccacc tcgacttca cggatacttt  1560
atccctgaga gaagaaggc ccagatcacc cactag                             1596

SEQ ID NO: 19           moltype = AA   length = 325
```

```
FEATURE                 Location/Qualifiers
source                  1..325
                        mol_type = protein
                        note = Fusarium fujikuroi
                        organism = unidentified
SEQUENCE: 19
MTTKYTSVHE SPNGPGDARP TASQIIDDYN LEGELSGKTV LVTGCSSGIG VETARAIYRT   60
GATLYLTARD VDKAKTVLPD LVDTSRVHFL HLDLNSLESV RGFAENFKSK STQLHILIEN  120
AGVMACPEGR TVDGFETQFG INHLAHFLLF YLLKDTLLNS STPAFNSRVV ILSSCAHQAG  180
SVHLNNLSLE GGYEPWKSYG QSKTANLWTA REIEKRFGAS GIHSWAVHPG SIATELQRHV  240
SDELKQKWAD DKEGAKLWKS TEQGAATTVL AAVSPELEGK GGLYLEDTQV AKPPARGMFG  300
VADWAYDEDG PSKLWAKSLE LLKLQ                                       325

SEQ ID NO: 20           moltype = DNA  length = 978
FEATURE                 Location/Qualifiers
misc_feature            1..978
                        note = Yarrowia codon-optimized FfRDH12
source                  1..978
                        mol_type = other DNA
                        organism = synthetic construct
SEQUENCE: 20
atgaccacta agtacacttc cgttcacgag tctcccaacg gccctggtga cgctcgaccc   60
accgcttccc agattatcga cgattacaac cttgagggag agctttctgg caagactgtt  120
ctcgtcaccg gctgttcctc tggtattggt gttgagactg cccgagctat ttaccgaact  180
ggtgccaccc tttacctcac tgcccgagat gtcgataagg ccaagaccgt tcttcccgac  240
cttgttgaca cttcccgagt ccactttctc caccttactc taactctctc ggagtctgtt  300
cgaggttttg ctgagaactt caagtctaag tccactcagc ttcacattct catcgagaac  360
gctggcgtga tggcctgtcc cgagggccga accgtcgatg gttttgagac tcagtttggt  420
atcaaccacc ttgctcactt tctcctcttt tacctcctca aggatacccct ctcaactct  480
tctcacccg ctttcaactc ccgagttgtc atcctctctc cttgtgctca caaggctagt  540
tccgttcacc ttaacaacct gtctcttgag ggtggataca agccttggaa gtcttacggc  600
cagtccaaga ctgccaacct ttggactgcc cgagagatcg agaagcgatt tggtgcttcc  660
ggtatccact cttgggctgt tcaccccggt tccatcgcta ctgagcttca gcgacacgtt  720
tccgacgagc ttaagcagaa gtgggctgac gataaggagg gtgccaagct gtggaagtcc  780
accgagcagg gtgccgccac cactgtcctt gctgctgttt ccctgagct tgagggtaag  840
ggcggtcttt accttgagga tacccaggtt gccaagcccc ctgcccgagg aatgtttggt  900
gttgctgact gggcttacga tgaggatggc ccctctaagc tctgggccaa gtctcttgag  960
ctccttaagc tccagtaa                                                978

SEQ ID NO: 21           moltype = AA  length = 525
FEATURE                 Location/Qualifiers
source                  1..525
                        mol_type = protein
                        note = Saccharomyces bayanus
                        organism = unidentified
SEQUENCE: 21
MNTYSEKTSL VQDECLAKMI QNGHSRRMGS VEDLYAALNR QKLYRNFSTY SELNDYCTKD   60
QLALALRNIC LKNPTLLHIV LPARWPDHEN YYLSSEYYSQ PHPKHDYISV LPELKFDGVI  120
LNEQPEHNAL MKQILEELKD SNGSYTAKIF KLTTALTIPY AGPTSPTWRL ICLPEEGYTD  180
KWKKFIFLSN HCMCDGRTSI HFFQDLRDEL NNIKTPPKKL DYIFQYEKDY QLLRKLPEPI  240
ENMIDFRPPY MFIPKSLISG FIYSHLRFSS KGVCTRMDEL EKNDDIVTEI ITISPSELQK  300
IRTKIKSNIP GKCTITPFLE VCWFVSLHKW GKFFKPLKFE WLTDVFIPAD CRSLLPEDED  360
VRAMYRYGAN VGFVDFTPWI SEFNMNDSKE NFWPLIAHYH EVISGAINDK KHLNGLGFNI  420
QGLVQKYVNI DKVMRDRALG KSRGGTLLSN VGIFHQSEET DSRYSIRDLA FGQFQGSWHQ  480
AFSLGVCSTN VKGMNIVISS TKNAVGSQEL LEELCAMYKA LLLDP                 525

SEQ ID NO: 22           moltype = DNA  length = 1578
FEATURE                 Location/Qualifiers
misc_feature            1..1578
                        note = Yarrowia codon-optimized SbATF1
source                  1..1578
                        mol_type = other DNA
                        organism = synthetic construct
SEQUENCE: 22
atgaacacct actctgagaa gacctctctt gttcaggacg agtgtctggc taagatgatt   60
cagaacggtc actctcgacg aatgggctct gtcgaggacc tttacgccgc cctcaaccga  120
cagaagctct accgaaactt ctctacttac tctgagctga cgattactg cactaaggat  180
cagctcgctc ttgctctccg aaacatttgt ctgaagaacc cactctcct tcacattgtt  240
cttcccgctc gatggcccga tcacgagaac tactaccttt cttctgagta ctactctcag  300
ccccaccccca agcacgatta catctctgtt cttcccgagc tgaagttcga tggtgtgatt  360
ctcaacgagc agcccgagca caacgccctt atgaagcaga ttcttgagga gcttaaggat  420
tccaacggtt cttacactgc taagatttc aagctcacta ccgctctcac tattcccac  480
gctggtccca ctctccccac ttggcgactg atttgtctgc ccgaggaggg atacaccgat  540
aagtggaaga agttcatttt ccttccaac cactgcatgt gtgatggtcg aacctctatt  600
cacttctttc aggatctccg agatgagctt aacaacatca agactcccc caagaagctc  660
gactacattt ccagtacgag gaaggactac cagcttctcc gaaagctccc cgagcccatt  720
gagaacatga ttgattttcg accccctac atgtttattc ccagtccct tatttccggc  780
ttcatttact cccaccttcg attctcctct aagggtgtgt gtacccgaat ggacgagctt  840
gagaagaaca cgatattgt tactgagatc atcacctatc tccctctga gcttcagaag  900
```

```
attcgaacta agatcaagtc taacattccc ggcaagtgca ccatcactcc cttccttgag   960
gtttgttggt ttgtttctct ccacaagtgg ggcaagtttt tcaagcccct caagttcgag  1020
tggcttaccg atgtttttat tcccgctgat tgccgatctc tgctccccga ggacgaggac  1080
gtgcgagcta tgtaccgata cggcgctaac gtcggttttg ttgacttcac tccctggatt  1140
tctgagttta acatgaacga ctctaaggag aacttctggc cccttattgc tcactaccac  1200
gaggttattt ctggtgccat caacgacaag aagcacctca acggtcttgg tttcaacatt  1260
cagggccttg tccagaagta cgtcaacatt gacaaggtga tgcgagatcg agcccttggt  1320
aagtcccgag gaggcaccct gctctctaac gtgggtattt tccaccagtc tgaggagact  1380
gactcccgat actctatccg agacctcgct ttcggtcagt tcagggttc ttggcaccag   1440
gctttctctc tcggtgtttg ttccactaac gtgaagggaa tgaacattgt tatttcttcc   1500
actaagaacg ccgtgggttc ccaggagctc cttgaggagc tttgtgccat gtacaaggct  1560
ctgctccttg acccctaa                                                1578

SEQ ID NO: 23          moltype = AA    length = 391
FEATURE                Location/Qualifiers
source                 1..391
                       mol_type = protein
                       note = Fragaria x ananassa
                       organism = unidentified
SEQUENCE: 23
MSYKNNHSIL SKPNDPVEVI RDALSKALQF YYPLAGRLRE GPNKKLMVDC TGEGILFVEA   60
NAEVTLDELG DAILPPCPFL DGFLFNVPGS DGILGSPLCL IQVTRLSCGG FIFALRLNHT  120
ICDALGLVQF LNAVGEIAQG KYAPSITPVW ERELLSARDP PRISCTHEEF DDSIDHSYPN  180
YGATVQQCYC FGPKEIKSLR EHLPPHLSTC SSTFELITAC VWKCRTISLD MDPEQIVRLS  240
CVVTALGKHN NVCLPLGYYG NTFTYPAVVS TAERLCNSPL GYAVELVKKS KAKMSEEYLR  300
SAIDFVEVRG RPPFALEGMS DFLVSDNTRT GLGEIDFGFG KPVYAGVAKS TDLISFYVRS  360
TNKEEREILV PVCLPILSME IFQQELKKMI G                                391

SEQ ID NO: 24          moltype = DNA    length = 1176
FEATURE                Location/Qualifiers
misc_feature           1..1176
                       note = Yarrowia codon-optimized FaATF
source                 1..1176
                       mol_type = other DNA
                       organism = synthetic construct
SEQUENCE: 24
atgtcttaca agaacaacca ctctattctg tctaagccta cgaccctgtc gaggtgatt    60
cgagatgccc tgtccaaggc ccttcagttt tactaccctc tcgctggacg actccgagag  120
ggtcccaaca agaagctcat ggtggactgc actggtgagg gaatcctctt tgttgaggct  180
aacgctgagg tcactctcga tgagctcggc gatgctatcc ttccccttg tccttttcctt  240
gacggttttc tctttaacgt gcccggttct gacggtattc ttggttctcc tctctgtctt  300
attcaggtca ctcgactctc ttgtggaggt tttatttttg ctctgcgact taaccacact  360
atttgcgatg ctctgggtct tgttcagttt ctcaacgctg ttggcgagat tgcccaggga  420
aagtacgctc cttctattac ccctgttggt gagcgagagc tcctctctgc ccgagaccct  480
ccccgaattt cctgtactca cgaggagttt gacgattcta ttgaccactc ttaccctaac  540
tacggtgcta ccgttcagca gtgttactgt tttggtccca aggagatcaa gtcccttcga  600
gagcaccttc cccctcacct ttctacttgt tcttccactt ctcagcttat tactgcttgt  660
gtgtggaagt gccgaactat ctctctcgat atggaccctg agcagattgt ccgactctct  720
tgcgttgtta ctgctcttgg taagcacaac aacgtttgtc tccctctcgg atactacgga  780
aacactttca cttaccctgc tgttgttcct actgccgagc gactttgtaa ctctcccctg  840
ggttacgctg tggagcttgt caagaagtcc aaggctaaga tgtctgagga gtaccttcga  900
tctgctattg actttgtcga ggttcgagga cgaccccct ttgctcttga gggtatgtct   960
gacttccttg tttccgataa cactcgaact ggtcttggtg agattgactt tggcttcgga  1020
aagcctgttt acgctggagt tgccaagtcc accgatctca tctcctttta cgtccgatcc  1080
actaacaagg aggagcgaga gattcttgtc cctgtttgcc ttcccattct gtctatggag  1140
atttttcagc aggagctcaa gaagatgatt ggttaa                           1176

SEQ ID NO: 25          moltype = AA    length = 219
FEATURE                Location/Qualifiers
source                 1..219
                       mol_type = protein
                       organism = Escherichia coli
SEQUENCE: 25
MEKKITGYTT VDISQWHRKE HFEAFQSVAQ CTYNQTVQLD ITAFLKTVKK NKHKFYPAFI   60
HILARLMNAH PEFRMAMKDG ELVIWDSVHP CYTVFHEQTE TFSSLWSEYH DDFRQFLHIY  120
SQDVACYGEN LAYFPKGFIE NMFFVSANPW VSFTSFDLNV ANMDNFFAPV FTMGKYYTQG  180
DKVLMPLAIQ VHHAVCDGFH VGRMLNELQQ YCDEWQGGA                        219

SEQ ID NO: 26          moltype = DNA    length = 660
FEATURE                Location/Qualifiers
misc_feature           1..660
                       note = Yarrowia codon-optimized EcCAT
source                 1..660
                       mol_type = other DNA
                       organism = synthetic construct
SEQUENCE: 26
atggagaaga agattactgg ttacaccact gtcgatattt ctcagtggca ccgaaaggag   60
cactttgagg cttttcagtc tgttgctcag tgtacttaca accagaccgt tcagctcgat  120
attaccgctt tccttaagac tgtcaagaag aacaagcaca gttttaccc tgcctttatt   180
```

```
cacattcttg cccgactgat gaacgctcac cctgagttcc gaatggctat gaaggatggt   240
gagctcgtga tttgggattc tgttcaccct tgttacaccg ttttcacga gcagactgag    300
actttctctt ccctctggtc tgagtaccac gatgacttcc gacagttcct tcacatttac   360
tctcaggatg tcgcctgtta cggtgagaac ctggcttact tccctaaggg ttttattgag   420
aacatgtttt tcgtgtctgc taaccccctgg gtttccttca cctcttttga ccttaacgtg   480
gctaacatgg acaacttctt cgcccccgtt ttcactatgg gaaagtacta cactcagggc   540
gacaaggtgc tcatgcccct ggccattcag gttcaccacg ctgtctgtga tggcttttcac  600
gtcggtcgaa tgcttaacga gcttcagcag tactgcgatg agtggcaggg cggcgcttag   660

SEQ ID NO: 27             moltype = AA   length = 363
FEATURE                   Location/Qualifiers
source                    1..363
                          mol_type = protein
                          organism = Euonymus alatus
SEQUENCE: 27
MMDAHQEIKN FIKVWVQAMV CLSYAYYFSS RLPKGLLRLL SLLPVLYLLL IAPLNISSFI   60
LSSITGFFLA WLTTFKVISF AFDQGPLYPL PQNLLHFISI ACLPITIKRN PSPKLKSTTN   120
PSPISHLLKK AFMSFPSKVL FHWVIAHLYQ YKKYMDPNVV LVIYCCHVYV MLDISLSLCA   180
TLAEFLCGFD VEPQFKEPYL ATSLQDFWGR RWNIIVSSVL RSTVYAPTRN IASYLIGSRW   240
AYFPAIIATF VVSGVMHDVV YYVYMMHMYP KWDMTGHFVL HGICEALEVE MKCKRSRSDK   300
WRRHPAVDWV MVMGFVMGTS VSLLFVPLLR DNVDQIVAEE YSILFNFVRE KIVMLGTRFV   360
CGN                                                                 363

SEQ ID NO: 28             moltype = DNA   length = 1092
FEATURE                   Location/Qualifiers
misc_feature              1..1092
                          note = Yarrowia codon-optimized EaCAcT
source                    1..1092
                          mol_type = other DNA
                          organism = synthetic construct
SEQUENCE: 28
atgatggatg ctcaccagga gatcaagaac ttcatcaagg tttgggtgca ggctatggtg   60
tgtctttctt acgcttacta cttctcctct cgacttccca agggactcct tcgacttctc   120
tctcttctcc ctgttcttta cctcctcctt atcgctcccc ttaacatttc ctctttcatt   180
ctttcttcta tcaccggctt cttccttgct tggcttacca cttcaaggt catctctttt   240
gctttcgatc agggtcctct ctaccctctc cctcagaacc tccttcactt catttccatt   300
gcttgtctcc ctatcactat caagcgaaac ccctctccta agctcaagtc caccactaac   360
ccttctccta tttctcacct tctcaagaag gcttttatgt cttttcccctc taaggttctt   420
ttccactggg tcattgctca cctttaccag tacaagaagt acatggaccc taacgtggtc   480
ctcgttatct actgttgtca cgtttacgtt atgcttgaca tttctctctc tctgtgtgct   540
accctggctg agtttctctg tggttttgac gttgagcctc agtttaagga gccttacctt   600
gctacttctc ttcaggactt ttgggccga cgatggaaca ttattgtctc ttctgtcctg   660
cgatccactg tttacgctcc cactcgaaac attgcttctt accttattgg atctcgatgg   720
gcttactttc ccgctattat tgctactttc gttgtgtctg gagttatgca cgatgtcgtg   780
tactacgttt acatgatgca catgtaccct aagtgggata tgactggtca cttcgtcctt   840
cacggaattt gtgaggctct ggaggtggag atgaagtgta agcgatctcg atctgacaag   900
tggcgacgac accctgctgt cgattgggtg atggtgggtt tttgtcat ggtagcttct   960
gtttccctcc tttcgtccc tctccttcga gataacgtcg atcagattgt tgctgaggag  1020
tactctattc tctttaactt tgttcgagag aagattgtca tgcttggtac tcgatttgtc  1080
tgtggaaact aa                                                     1092

SEQ ID NO: 29             moltype = AA   length = 459
FEATURE                   Location/Qualifiers
source                    1..459
                          mol_type = protein
                          organism = Malus domestica
SEQUENCE: 29
MMPFSVLQVK RLQLELITPA KPTLQEAKFL SDIDDQEGLR FQVPVIMCYK DNPSLNKNCN   60
PVKVIREALS RALVYYYPLA GRLKEGPNRK LMVDCNGEGI LFVEASADVT LEQLGDKILP   120
PCPLLEEFLF NFPGSDGIIG CPLLLVQVTC LTCGGFILAL RVNHTMCDAP GLLLFLTAIA   180
EMARGAHAPS ILPVWERELL FSRDPPRITC AHHEYEDVID HSDGLYASSN QSNMVQRSFY   240
FGAKEMRVLR KQIPPHLIST CSTFDLITAC LWKCRTLALN INPKEAVRVS CIVNARGKHN   300
NVRLPLGYYG NAFAFPPAAIS KAEPLCKNPL GYALELVKKA KATMNEEYLR SVADLLVLRG   360
RPQYSSTGSY LIVSDNTRAG FGDVNFGWGQ PVFAGPAKAL DLISFYVQHK NNTEDGILVP   420
MCLPSSAMER FQQELERITQ EPKEDICNNL RSTRIMSMM                         459

SEQ ID NO: 30             moltype = DNA   length = 1380
FEATURE                   Location/Qualifiers
misc_feature              1..1380
                          note = Yarrowia codon-optimized MdATF
source                    1..1380
                          mol_type = other DNA
                          organism = synthetic construct
SEQUENCE: 30
atgatgccct ctctgttct ccaggttaag cgacttcagc ttgagcttat acccctgcc    60
aagcccactc tccaggaggc taagtttctc tctgacatcg acgatcagga gggccttcga   120
tttcaggttc ctgtcattat gtgttacaag gataaccctt ctcttaacaa gaactgtaac   180
cctgttaagg tgattcgaga ggctcttccc gagctcttg tttactacta ccctctcgct   240
ggacgactta aggagggtcc taaccgaaag ctcatggtcg attgcaacgg tgagggtatt   300
```

```
ctgttcgttg aggcttctgc tgatgttacc cttgagcagc ttggtgataa gattcttccc  360
ccttgtcctc tccttgagga gttccttttc aactttcccg ttctgatgg tattattggt  420
tgtcctctcc ttctcgttca ggtcacttgc cttacctgtg gaggctttat tcttgccctt  480
cgagtcaacc acactatgtg tgatgctcct ggtctgctcc tgttcctgac cgccatcgct  540
gagatggccc gaggagctca cgctccttct attcttcccg tttgggagcg agagcttctc  600
ttttcccgag atccccctcg aattacttgt gctcaccacg agtacgagga cgttattgac  660
cactctgacg gtctttacgc ttcttccaac cagtctaaca tggttcagcg atctttctac  720
tttggtgcca aggagatgcg agttcttcga agcagattc ctccccacct tatttctacc  780
tgctctacct ttgaccttat taccgctttgt ctttggaagt gtcgaaccct tgctcttaac  840
attaaccctta aggaggctgt tcgagtttct tgcattgtta acgcccgagg aaagcacaac  900
aacgttcgac ttcccccttgg ttactacgga aacgctttg cttttcccgc tgctatctct  960
aaggccgagc ctctctgtaa gaaccccctt ggttacgctc ttgagcttgt caagaaggct  1020
aaggctacta tgaacgagga gtaccttcga tctgtggcta atctccttgt tcttcgagga  1080
cgacctcagt actcttctac cggatcttac cttattgttt ctgataacac ccgagctgtt  1140
tttggtgatg ttaactttgg ttggggacag cccgttttgt ctggacccgc caaggccctt  1200
gaccttattt ccttctacgt tcagcacaag aacaacactg aggatggtat tcttgttcct  1260
atgtgtctcc cttcctccgc tatggagcga tttcagcagg agcttgagcg aattactcag  1320
gagcctaagg aggatatttg taacaaccctt cgatctactc gaatcatgtc tatgatgtaa  1380

SEQ ID NO: 31            moltype = AA   length = 465
FEATURE                  Location/Qualifiers
source                   1..465
                         mol_type = protein
                         note = Petunia x hybrida
                         organism = unidentified
SEQUENCE: 31
MCPKLARINS YMGNTDFHVT VKKKEVVAAV LPMHHEHWLP MSNLDLLLPP LDFGVFFCYK   60
RSKINNDTKD DDETIKKALA ETLVSFYALA GEVVFNSLGE PELLCNNRGV DFFHAYADIE  120
LNNLDLYHPD VSVHEKLIPI KKHGVLSVQV TGLKCGGIVV GCTFDHRVAD AYSANMFLVA  180
WAAIARKDNN INTVIPSFRR SLLNPRRPPQ FDDSFIDSTY VFLSSPPKQP NDVLTSRVYY  240
INSQEINLLQ SQATRNGSKR SKLECFSAFL WKTIAEGGID DSKRCKLGIV VDGRQRLRHD  300
SSTTMKNYFG NVLSVPYTEA SVGQLKQTPL GKVADLVHTC LDNVANEHHF PSLIDWVELH  360
RPRQAIVKVY CKDECNDEAA IVVSSGLRFP LSQVNFGWGC PDFGSYIFPW GGQTGYVMPM  420
PSPNKNGDWI VYMHLQKKHL DLVETRAPHI FHPLTACYLD LTATY                 465

SEQ ID NO: 32            moltype = DNA   length = 1398
FEATURE                  Location/Qualifiers
misc_feature             1..1398
                         note = Yarrowia codon-optimized PhATF
source                   1..1398
                         mol_type = other DNA
                         organism = synthetic construct
SEQUENCE: 32
atgtgcccta agctcgctcg aattaactct tacatgggaa acactgactt tcacgttacc   60
gtcaagaaga aggaggttgt ggctgctgtt ctccctatgc accacgagca ctggcttccc  120
atgtccaacc ttgaccttct ccttccccct ctcgactttg tgttttctt ctgctacaag  180
cgatctaaga ttaacaacga taccaaggat gacgatgaca ctattaagaa ggctcttgct  240
gagactctcg tttctttta cgctcttgct ggagaggtgg ttttcaactc tctcggagag  300
cccgagcttc tctgtaacaa ccgaggagtt gatttctttc acgcttacgc tgatattgag  360
ctcaacaacc ttgaccttta ccaccccgat gtctctgttc acgagaagct gattcctatc  420
aagaagcacg gcgttctctc tgttcaggtc actggcctta agtgtggagg tatcgttgtt  480
ggatgcactt tcgatcaccg agttgctgat gcttactctg ctaacatgtt ccttgttgct  540
tgggctgcta ttgctcgaaa ggataacaac attaacactg ttatccccttc tttccgacga  600
tccctcctta accctgacg acctccccag tttgacgatt cctttatcga ctccacctac  660
gttttccttt cttctccccc taagcagcct aacgatgtcc ttacttcccg agtgtactac  720
attaactctc aggagattaa cctccttcag tctcaggcta ctcgaaacgg atctaagcga  780
tctaagctgg agtgttttct cgcctttctc tggaagacta ttgctgaggg aggtattgac  840
gattctaagc gatgtaagct cggaattgtt gtcgatggcc gacagcgact gcgacacgac  900
tcttctacca ccatgaagaa ctactttggc aacgttctt ctgttcctta cactgaggct  960
tctgttggac agctcaagca gactccccctt ggtaaggttc ctgaccttgt tcacacttgc  1020
ctcgataacg ttgctaacga gcaccactt ccctctctca ttgactggg tgagcttcac  1080
cgacctcgac aggctattgt taaggtttac tgtaaggatg agtgtaacga tgaggctgcc  1140
atcgttgtct cctctggact ccgattccc cttctcagg ttaactttgg ctggggctgt  1200
cctgacttg gctcttacat ttccccttgg ggcggtcaga cggttacgt gatgcctatg  1260
ccttctccca caagaacgg tgattggatt gttacatgc accttcagaa gaagcacctt  1320
gaccttgtcg agactcgagc ccctcacatc ttccacccc ttaccgcttg ttacctcgat  1380
ctcactgcta cttactaa                                                1398

SEQ ID NO: 33            moltype = AA   length = 559
FEATURE                  Location/Qualifiers
source                   1..559
                         mol_type = protein
                         organism = unidentified
SEQUENCE: 33
MGDLDARGTS AHPELSERPS IMPSMSDIQD PSGDDKATPR GSAAGLPQLE LAGHARRLGH   60
LENFFAVQHR QQIYSSFAVF CEFDTACSLA QLASAVRNVC LSNPLLLHTV EPKHPDIAGF  120
YHSDEYLSRP WPQHDYMRVL REVHVADVVM NGQKEHAHVV RDAVDVFQAH GNQVTSELLE  180
LMTQIEIPHA SQTRPSWRLL CFPHGEANRW RTFAFVSNHC SSDGLSGLNF FRDLQKELAH  240
GPTSGAPGAP GASGVIFDYA QDAATLPKLP PPIDQKLDYR PSKKALLGLL AGKFVREKLG  300
```

```
YVSAAPPTTP TSDLAHPEGH QYYCYLVNVP TSSVAHIKTQ VRENVPHKCT LTPFLQACWL    360
VSLFKYGRVF SGSWLERYTD VLVAMNTRQL LPEDLELQRQ YRYGSNVGGV RYNYPIAPLD    420
VRDNDQKFWS LVESYRLALS DARDKNDYLY ALGALMLPEI YEKKNVDAVV NDTILNQRRS    480
GTLISNVGYV RDEQPTAFAI KNHVFSQGVG ANRNAFVLNI CATDQGGLNI AISIAKGTLA    540
SRQEGQELCD IFKSTLLRF                                                559

SEQ ID NO: 34            moltype = DNA  length = 1680
FEATURE                  Location/Qualifiers
source                   1..1680
                         mol_type = other DNA
                         organism = unidentified
SEQUENCE: 34
atgggtgatc tcgacgcgag gggaacatca gcgcacccgg agctctcgga gaggccaagc     60
atcatgccct cgatgtcgga tatccaggac ccaagcggtg acgacaaggc cacgcccgc     120
ggctccgccg cggggctgcc gcagctcgag ctcgccggcc acgcccggcg cctgggccat    180
ttggagaatt tcttcgccgt ccagcaccgg cagcagatct attccagttt cgccgtgttc    240
tgcgagttcg acaccgcgtg ctcgctcgcg cagctcgcgt ccgctgtgcg aaacgtgtgt    300
ctttcgaacc cgctgctgct gcacaccgtc gagcccaagc accggacgat cgccggcttc    360
taccactccg acgaatatct gtcccgaccc tggcccagc acgactacat gcgcgttttc    420
cgcgaggtcc acgtcgccga cgtggtgatg aacggccaga agagcacgc gcatgtcgtg    480
cgcgacgccg tcgacgtttt ccaagcgcat ggaaaccagg tcaccagcga gctgctcgag    540
ctcatgaccc agattgagat cccgcacgct cccaaacga gacccagctg gaggttgctg    600
tgtttcccac acggcgaggc caaccggtgg cgcacgtttg cgtttgtatc caatcattgt    660
tccagcgacg tctctcgggg tctgaacttc tttcgggacc tgcaaaagga gctcgcgcac    720
ggccccacct cggggccc cggggccccg gggcctccg cgtcatctt cgactacgcc        780
caggacgccg caacactgcc caaactgccg ccacccattg accaaaact cgattaccgt    840
ccgtccaaga aggccttttt gggactttg gccggcaagt tcgtgcgtga aaaactcggc    900
tacgtatcgg ccgcccgcc aacgacccg acctccgatt tggcgcaccc agaaggtcac    960
caatactact gctaccttgt aaacgtaccg acatctagtg tggcccacat caaaacgcaa  1020
gtgcgcgaaa atgcccgca caaatgcacg ctgacgcgat tcttacaggc atgctggctc   1080
gtgtcactgt tcaagtatgg tcgcgttttt tccggctcct ggctcgaacg atacacggac   1140
gttctcgtcg ctatgaacac ccggcaactg ttgcccgaag atttggaatt gcaacgccag   1200
taccgttacg gtagtaacgt gggaggggta cgttacaatt atccaatcgc accgctcgac   1260
gtccgcgaca acgaccagaa attctggtcc ctggttggaga gttaccgact ggcccttagc   1320
gacgcacgcg acaaaaatga ttacttgtac gcattggtg ctctaatgct tccagagatc   1380
tacgaaaaaa aaaacgtcga tgctgtggtc aatgacacaa ttctgaacca gcgtcgttcc   1440
ggaacgttga tcagtaacgt cggctacgtg cgcgatgaac agcccactgc gtttgcaatt   1500
aagaatcatg tcttttcaca aggcgttggc gccaacagaa acgcatttgt gcttaacata   1560
tgtgccacgg accaaggcgg cctaaatatc gccatcagta tcgccaaggg aaccttggcg   1620
tctcgtcaag aaggccaaga actttgcgac atctttaaat caacgttact gcgattctaa   1680

SEQ ID NO: 35            moltype = DNA  length = 1680
FEATURE                  Location/Qualifiers
misc_feature             1..1680
                         note = Yarrowia codon optimized LmATF1
source                   1..1680
                         mol_type = other DNA
                         organism = synthetic construct
SEQUENCE: 35
atgggtgatc tcgatgcccg aggaaccctct gctcaccccg agctctctga gcgaccttct     60
attatgcctt ctatgtctga tattcaggac ccttctggtg atgacaaggc tactcccgga    120
ggatctgctc ctgggctgcc ccagcttgag cttgctggac acgcccgacg acttggccac    180
cttgagaact tctttgctgt ccagcaccga cagcagattt actcttcttt tgctgttttt    240
tgtgagtttg acactgcttg ttctctcgct cagcttgctt ctgctgtgcg aaacgttttgt   300
ctttctaacc cccttctcct tcacactgtt gagcctaagc accgtggatcc cgctggattc    360
taccactctg acgagtacct ttcccgaccc tggcctcagc acgattacat gcgagttctt   420
cgagaggttc acgtcgctga cgttgttatg aacggacaga aggagcacgc tcacgttgtt    480
cgagatgctg ttgacgtttt tcaggctcac ggaaaccagg ttacttctga gctccttgag    540
cttatgactc agattgagat tcctcacgct ctcagactc gaccctcttg gcgacttctc    600
tgttttcccc acggagaggc taaccgatgg cgaacctttg cttttgtttc taaccactgt    660
tcttctgatg tctttctgg tcttaacttc tttcgagatc tccagaagga gcttgctcac    720
ggcccccacct ctggtgctcc tggtgccccc ggagcttccg gagttatttt cgattacgct    780
caggacgctg ctaccctgcc caagctgccc cctccattg atcagaagct cgattaccga    840
ccttctaaga aggctcttct cggcctttct gctggcaagt tcgttcgaga gaagctcggt    900
tacgtttctg ctgctcctcc cactacccct acctctgacc ttgctcaccc tgagggtcac    960
cagtactact gttaccttgt taacgttccc acttcttctg ttgcccacat taagactcag   1020
gtgcgagaga acgttcctca caagtgtact ctcactcct ttctccaggc ttgttggctt   1080
gtttctctgt tcaagtacgg tcgagttttt tctggttctt ggctctgagcg atacaccgat   1140
gttcttgttg ctatgaacac ccgacagctt cccccgaag acctcgagct tcagcgacag   1200
taccgatacg gttctaacgt tggaggtgtt cgatacaact acccctattgc tcccccttgac   1260
gttcgagata cgatcagaa gttctggtcc cttgttgagt cttaccgact gcccctttct   1320
gatgcccgag ataagaacga ttaccttttac gctcttggtg ctcttatgct ccctgagatt   1380
tacgagaaga agaacgttga tgctgttgtt aacgatacca ttcttaacca gcgacgatct   1440
ggaaccctta tcagcaacgt tggttacgtt cgagatgaac agcccactgc gtttgctatt   1500
aagaaccacg ttttttctca gggagttgga gctaaccgaa acgcttttgt tcttaacatt   1560
tgtgctaccg atcagggtgg tcttaacatc gctatttcta ttgctaaggg aacccttgct   1620
tctcgacagg agggacagga gctttgtgat atttttaagt ctactctcct tcgattttaa   1680

SEQ ID NO: 36            moltype = AA  length = 536
```

```
FEATURE              Location/Qualifiers
source               1..536
                     mol_type = protein
                     note = Lachancea fermentata
                     organism = unidentified
SEQUENCE: 36
MIIILTKPKF PSSNSRSLEI KLNNMPPGTL LREMIENGHA RPMGSIENIY GIFNRQKLYR  60
NFSMFAEIND FCNERQLRAA LRNLCLKNPI LLHTIVPEIW PFNEKYYLSD EYYCMPRSQH 120
EFIAILPELD LSDILANKQT QYQQVLEKAF REFESSNFCY TSEVYKLIAT ISIPYVGPSW 180
RLICLPEKRG TEWRKFIFIS NHCLCDGRSA ANFFHDLKEE LNCNIDNRLT VTTIFSYERD 240
HYLLPKLPEP LEKRIDFRPP WSYFPKYLVW EPIVNHFKFS SNCATSRLDE SFDGKTLLTE 300
IINIDVQVLE KVRQLIKANV HEGGTITPFL EICWLISLHK WGAFSGKSWT KCLTDVFVPV 360
DVRNLLPDDD DIRKSYRYGC NVAAIELNPW ISQLDVEKNS DEFWALVSQN QNKITSLLQK 420
KEQLNLIGFN TLDIVEKNFN LDRELCVHTL NKPRQGTLLS NLGIFPQNSQ ERDRYSLENL 480
IFGQFQGSFR ESFSMCVCST DRKGMNIVLT TTSDLIPNSK SWEDLCSTFK SIISDT     536

SEQ ID NO: 37        moltype = DNA  length = 1611
FEATURE              Location/Qualifiers
misc_feature         1..1611
                     note = Yarrowia codon optimized LfATF1
source               1..1611
                     mol_type = other DNA
                     organism = synthetic construct
SEQUENCE: 37
atgatcatta ttctcactaa gcctaagttc ccttcctcca actctcgatc cctggagatc   60
aagctgaaca acatgccccc tggtactctc ctgcgagaga tgatcgagaa cggacacgcc  120
cgacctatgg gctccattga aacatttac ggaattttta accgacagaa cgttctacga  180
aactttcta tgtttgccga gatcaacgac ttttgtaacg agcgacagct tcgagccgcc  240
ctgcgaaacc tgtgtcttaa gaaccctatt ctccttcaca ccattgtccc cgagatttgg  300
cctttcaacg agaagtacta cctgtctgac gagtactact gtatgcctcg atctcagcac  360
gagtttatcg ctattctgcc cgagctcgac ctgtccgata ttctggccaa caagcagacc  420
cagtaccagc aggttctgga aaggcttttc gagagttcg agtcctccaa cttttgttac  480
acctctgagg tgtacaagct gattgctact atttctatcc cttacgtggg cccctcttgg  540
cgacttattt gcctccctga aagcgaggga accgagtggc gaaagttcat cttcatttcc  600
aaccactgtc tctgtgatgg tcgatccgcc gccaactttt tccacgacct gaaggaggag  660
ctgaactgta acattgacaa ccgacttacc gtcactacca ttttctctta cgagcgagat  720
cactaccttc tccccaagct gcccgagccc ctggagaagc gaattgattt ccgacccgct  780
tggtcttact ttcccaagta ccttgtctgg agcccatcg tgaaccactt caagttctcc  840
tctaactgcg ctacttcccg actcgatgag tcttttcgacg taagactct ccttaccgag  900
attattaaca ttgacgtgca ggtccttgag aaggttcgac agctcatcaa ggccaacgtg  960
cacgagggtg gtactatcac cccttttcctt gagatttgtt ggctcatttc ccttcacaag 1020
tggggagctt tctctggtaa gtcctggact aagtgcctca ccgatgtttt tgttcccgtc 1080
gatgtccgaa accttctccc tgacgacgat gacatccgaa agtcttaccg atacggctgt 1140
aacgttgctg ctatcgagct taacccttgg atctctcagc tcgatgtcga agaactcc  1200
gatgagtttt gggcccttgt ttcccagaac cagaacaaga tcacctcccct cctccagaag 1260
aaggagcagc tcaacctcat tggctttaac accctcgata ttgtcgagaa gaactttaac 1320
ctcgaccgag agctctgcgt tcacactctc aacaagcccc gacagggtac tctcctgtcc 1380
aacctgggta ttttccctca gaactcccga gagcgagatc gatactccct ggagaacctg 1440
attttttggtc agtttcaggg ttccttccga gagtcttttct ctatgtgtgt ctgttccacc 1500
gatcgaaagg gaatgaacat tgttctcacc actacctctg atctcatccc caactccaag 1560
tcctgggagg acctttgctc taccttcaag tctattatct ccgacactta g           1611

SEQ ID NO: 38        moltype = AA  length = 515
FEATURE              Location/Qualifiers
source               1..515
                     mol_type = protein
                     note = Lachancea fermentata
                     organism = unidentified
SEQUENCE: 38
MYESLQTLIE RGHARRLGHV ENYFVLAQRQ DLYRVFAYYG EFGEPCSLRQ LTQALRSMCL  60
QQPVLLCQVK PQERPDLELY YRSEEYLSTP GQDRDYIALA NKVRISDVLI NNQTEYAEVM 120
HKVMEEYEAN GHNFTSKIFE ILAPIRISHT DPNKLNWRLL ALPGEIPGEW NKFVFLSNHI 180
LKDGSSGAHF FIDLKDSLNS LPSDLQDTDR IFDYKSDYKF VKEIPVPIDE VLDYKPNLKQ 240
IANVFSTQLV REKLGYLSPA PTITRYTDAE NNTNEYHTCF INFTPEEVDS IKKKIKDRAG 300
PSCTMTPFLQ ACWLVSLYKS GKVFTKSFKE WFVDMMIPMY TPQMLSDGEQ TRADYRYGCN 360
VGGTRYNYLI SSLNVGNNSK KFWKLVSYYN DVFRDSKASN SYLYLIGMIM LDPAWKEKNL 420
DATVLQNLLG RHRQGTVLSN VGFFSVNGEP QDAFHLKNLL FTQTVGSYTF AFNLNVCSTD 480
VAGMNVGASV SKGTLPTRND WEELCEIFKT TVLQM                            515
```

```
SEQ ID NO: 39              moltype = DNA  length = 1548
FEATURE                    Location/Qualifiers
misc_feature               1..1548
                           note = Yarrowia codon optimized LffATF1
source                     1..1548
                           mol_type = other DNA
                           organism = synthetic construct
SEQUENCE: 39
atgtacgagt cccttcagac tctcatcgag cgaggacacg ctcgacgact cggccacgtg    60
gagaactact ttgttctcgc tcagcgacag gatctctacc gagttttcgc ttactacgga   120
gagttcggag agccttgctc ccttcgacag ctcactcagg ccctccgatc tatgtgtctt   180
cagcagcctg ttctgctctg ccaggtcaag ccccaggagc gaccgacct cgagctttac    240
taccgatctg aggagtacct gtctactccc ggacaggagt gagattacat cgctcttgct   300
aacaaggtgc gaatctccga tgtccttatc aacaaccaga ctgagtacgc tgaggtcatg   360
cacaaggtta tggaggagta cgaggctaac ggccacaact ttacctctaa gattttgag    420
attctcgccc ctattcgaat ctctcacacc gatcccaaca agctgaactg gcgactcctt   480
gctcttcccg gagagatccc tggtgagtgg aacaagtttg tcttcctttc aaccacatt    540
cttaaggatg gctcctctgg cgctcacttt ttcattgatc tcaaggattc tctgaactct   600
ctcccttctg acctcaggga taccgaccga attttcgatt acaagtccga ctacaagttt   660
gttaaggaga tccccgtccc tatcgatgag gttcttgact acaagcctaa ccttaagcag   720
attgctaacg tcttttctac tcagcttgtt cgagagaagc tgggttacct ctctcctgct   780
cctaccatta ctcgatacac cgatgctgag aacaacacta acgagtacca cacttgcttt   840
attaacttta cccctgagga ggttgattct atcaagaaga agattaagga tcgagccgac   900
ccttcttgca ctatgacccc tttccttcag gcttgctggc tggtttccct ttacaagtcc   960
ggcaaggttt tcactaagtc tttcaaggag tggttcgtgg acatgatgat ccctatgtac  1020
acccccagag tgctctctga cggcgagcag acccgagctg actaccgata cggctgtaac  1080
gttggaggta ctcgatacaa ctacctcatc tcctctctta acgttggaaa caactccaag  1140
aagttttgga agctggtttc ttactacaac gatgtcttcc gagactctaa ggcctccaac  1200
tcttaccttt accttatcgg aatgatcatg cttgaccctg cttggaagga aagaacctg    1260
gacgccactg tccttcagaa cctccttggt cgacaccgac agggcactgt tctgtctaac  1320
gttggattct tttctgtgaa cggagagccc caggatgctt ttcaccttaa gaaccttctc  1380
tttacccaga ctgttggttc ttacaccttt gctttcaacc tcaacgtctg ctctactgac  1440
gtggccggaa tgaacgttgg cgcttctgtg tctaagggca ccctgcccac tcgaaacgac  1500
tgggaggagc tttgcgagat cttcaagact accgttctcc agatgtaa               1548

SEQ ID NO: 40              moltype = DNA  length = 23
FEATURE                    Location/Qualifiers
misc_feature               1..23
                           note = primer MO11984
source                     1..23
                           mol_type = other DNA
                           organism = synthetic construct
SEQUENCE: 40
agtacataca gtcgtcgtag tgc                                            23

SEQ ID NO: 41              moltype = DNA  length = 32
FEATURE                    Location/Qualifiers
misc_feature               1..32
                           note = primer MO11985
source                     1..32
                           mol_type = other DNA
                           organism = synthetic construct
SEQUENCE: 41
cacacggtct caccgttttt ctgggccttg ag                                  32

SEQ ID NO: 42              moltype = DNA  length = 46
FEATURE                    Location/Qualifiers
misc_feature               1..46
                           note = primer MO11986
source                     1..46
                           mol_type = other DNA
                           organism = synthetic construct
SEQUENCE: 42
cacacggtct caacggcatt cctttattat ctggcttaca actaca                   46

SEQ ID NO: 43              moltype = DNA  length = 38
FEATURE                    Location/Qualifiers
misc_feature               1..38
                           note = primer MO11987
source                     1..38
                           mol_type = other DNA
                           organism = synthetic construct
SEQUENCE: 43
cacacggtct cagtactact ccggtgacaa ggatttcc                            38
```

BIOSYNTHESIS OF RETINOIDS

This application is the continuation of U.S. application Ser. No. 16/647,730, 371 (c) date 16 Mar. 2020, which is the U.S. national phase of International Application No. PCT/EP2018/076033 filed 25 Sep. 2018, which designated the U.S. and claims priority to CH Patent Application No. 00715/18 filed 5 Jun. 2018, EP Patent Application No. 18168564.5 filed 20 Apr. 2018, and claims the benefit of U.S. Application No. 62/562,712 filed 25 Sep. 2017, U.S. Application No. 62/562,699 filed 25 Sep. 2017, U.S. Application No. 62/562,672 filed 25 Sep. 2017, and U.S. Application No. 62/562,602 filed 25 Sep. 2017, the entire contents of each of which are hereby incorporated by reference.

The content of the electronically submitted sequence listing (Name: 4662_4525_Sequence_Listing.xml; Size: 87,236 bytes; and Date of Creation: Jan. 29, 2023) filed with the application is incorporated herein by reference in its entirety.

The present invention is related to a novel enzymatic process for production of retinoids via a multi-step process, which process includes the use of heterologous enzymes having activity in a carotene-producing host cell, particularly wherein such process results in high percentage of retinoids, in trans-isoform.

Retinoids, including vitamin A, are one of very important and indispensable nutrient factors for human beings which have to be supplied via nutrition. Retinoids promote well-being of humans, inter alia in respect of vision, the immune system and growth.

Current chemical production methods for retinoids, including vitamin A and precursors thereof, have some undesirable characteristics such as e.g. high-energy consumption, complicated purification steps and/or undesirable by-products. Therefore, over the past decades, other approaches to manufacture retinoids, including vitamin A and precursors thereof, including microbial conversion steps, which would be more economical as well as ecological, have been investigated.

In general, the biological systems that produce retinoids are industrially intractable and/or produce the compounds at such low levels that commercial scale isolation is not practicable. There are several reasons for this, including instability of the retinoids in such biological systems or the relatively high production of by-products.

Thus, it is an ongoing task to improve the product-specificity and/or productivity of the enzymatic conversion of beta-carotene into vitamin A. Particularly, it is desirable to optimize the productivity and selectivity of enzymes involved in conversion of precursors and/or intermediates.

Surprisingly, we now could identify a process for production of retinyl esters, particularly retinyl acetate, using a modified host organism, such as a carotenoid-producing host cell, particularly fungal host cell, comprising and expressing genes involved in the conversion of beta-carotene to retinyl acetate, with a total conversion of at least about 10% towards generation of retinol and with a percentage of trans-retinyl acetate of at least 65%.

In particular, the present invention is directed to a host cell, particularly a carotenoid-producing host cell, such as a fungal host cell, comprising (1) a stereoselective/trans-selective beta-carotene oxidase (BCO) catalyzing the conversion of beta-carotene to a retinal mix with a percentage of at least 65% present as trans-retinal, and (2) acetyl transferases (ATFs) catalyzing the conversion of retinol to a retinyl acetate mix with a total conversion of at least 10% of retinol acetylated into retinyl esters, particularly retinyl acetate and wherein the ATFs have a preference for acetylation of trans-retinol. Preferably, at least 80% of the retinyl esters are in the form of retinyl acetate, preferably as trans-retinyl acetate.

A carotenoid-producing host cell, particularly fungal host cell, according to the present invention is optionally furthermore comprising (3) (preferably heterologous) retinol dehydrogenase (RDH) which is capable of converting retinal into retinol, particularly with a total conversion of at least about 90% towards generation of retinol.

A carotenoid-producing host cell, particularly fungal host cell, according to the present invention is optionally furthermore comprising (4) a modification in the endogenous acyltransferase activity, i.e. activity towards acylating retinol into long chain retinyl esters, said modification leading to reduction or abolishment of said endogenous acyltransferase activity.

As used herein, the term "fungal host cell" includes particularly yeast as host cell, such as e.g. *Yarrowia* or *Saccharomyces*.

As used herein, the terms "stereoselective", "selective", "trans-selective" or "trans-isomer selective" enzyme with regards to BCO are used interchangeably herein. They refer to enzymes, i.e. BCOs as disclosed herein, with increased catalytic activity towards trans-isomers, i.e. increased activity towards catalysis of beta-carotene into trans-retinal. An enzyme according to the present invention is trans-specific, if the percentage of trans-isoforms, such as e.g. trans-retinal, is in the range of at least about 65% based on the total amounts of retinoids produced by such an enzyme or such carotene-producing host cell, particularly fungal host cell, comprising/expressing such enzyme.

As used herein, the terms "beta-carotene oxidizing enzyme", "beta-carotene oxygenase", "enzyme having beta-carotene oxidizing activity" or "BCO" are used interchangeably herein and refer to enzymes which are capable of catalyzing the conversion of beta-carotene into retinal in a trans-isomer selective way, leading to a retinal mix with at least about 65%, such as e.g. 68, 70, 75, 80, 85, 90, 95, 98% or up to 100%, of retinal in trans-isoform, based on the total amount of retinoids including retinal produced by said host cell.

Trans-selective BCOs as defined herein might be obtained from any source, such as e.g. plant, animal, bacteria, fungi, algae. Particular useful stereoselective BCOs are obtained from fungi, in particular Dikarya, including but not limited to fungi selected from Ascomycota or Basidiomycota, preferably obtained from *Fusarium* or *Ustilago*, more preferably isolated from *F. fujikuroi* or *U. maydis*, such as e.g. FfCarX (polypeptide sequence derived from AJ854252), UmCCO1 (polypeptide sequence derived from EAK81726). Furthermore, particularly useful stereoselective BCOs are obtained from insects, in particular Diptera, preferably obtained from *Drosophila*, more preferably from *D. melanogaster*, such as e.g. DmNinaB or DmBCO (polypeptide sequence derived from NP_650307.2). Furthermore, particularly useful stereoselective BCOs are obtained from plants, in particular Angiosperms, preferably obtained from *Crocus*, more preferably from *C. sativus*, such as e.g. CsZCO (polypeptide sequence derived from Q84K96.1). Furthermore, particularly useful stereoselective BCOs are obtained from eukaryotes, in particular pesces, preferably obtained from *Danio* or *Ictalurus*, more preferably from *D. rerio* or *I. punctatus*, such as e.g. DrBCO1, IpBCO (polypeptide sequence derived from XP_017333634).

Thus, in one aspect the present invention is directed to a carotenoid-producing host cell, particularly a fungal host cell, used for biosynthesis of retinoids including vitamin A, said host cell comprising a polypeptide with at least 60%, such as e.g. 65, 70, 75, 80, 85, 90, 95, 97, 98, 99% or up to 100% identity to a polypeptide known from the database selected from the group consisting of SEQ ID NOs:1, 3, 5, 7 or polynucleotides encoding such sequences, or a polypeptide with at least 50%, such as e.g. 55, 60, 65, 70, 75, 80, 85, 90, 93, 95, 97, 98, 99% or up to 100% identity to a polypeptide according to SEQ ID NOs:9, 11, 13, 15, 17 or polynucleotides encoding such sequences.

Besides the stereoselective BCO as described above, which is preferably heterologous expressed in the carotene-producing host cell, particularly fungal host cell, as defined herein, the host cell furthermore comprises (2) acetyl transferases (ATFs) catalyzing the conversion of retinol to a retinyl acetate mix with a total conversion of at least 10% of retinol acetylated into retinyl esters, particularly retinyl acetate and wherein the ATFs have a preference for acetylation of trans-retinol.

As used herein, the terms "acetyl transferase", "retinol acetylating enzyme", "enzyme having retinol acetylating activity" or "ATE" are used interchangeably herein and refer to enzymes [EC 2.3.1.84] which are capable of catalyzing the conversion of retinol into retinyl acetate with an amount of at least 80%, about 87, 90, 92, 95, 97, 99 or up to 100% of produced retinyl acetate in the trans-isoform. Said ATFs are capable of converting retinol, preferably trans-retinol, into retinyl ester, particularly retinyl acetate, with a total conversion of at least about 10%, preferably 12, 15, 20, 30, 40, 50, 80, 90 or even 100% (based on the total amount of retinoids within the retinoid mix produced by said host cell) towards generation of retinyl esters, e.g. retinyl acetate. A preferred isoform is ATF1.

ATFs as defined herein might be obtained from any source, such as e.g. plants, animals, including humans, algae, fungi, including yeast, or bacteria. Particular useful ATFs, preferably ATF1 enzymes, are obtained from yeast, in particular *Saccharomyces* or *Lachancea*, preferably obtained from *Saccharomyces bayanus*, such as e.g. SbATF1 (polypeptide sequence derived from AHX23958.1), *Lachancea mirantina* (LmATF1; SEQ ID NO:33), or *Lachancea fermentati* such as LfATF1 (polypeptide sequence derived from SCW02964.1) or LffATF1 polypeptide sequence derived from LT598487). Furthermore, particularly useful ATF1 enzymes are obtained from plants, including but not limited to plants selected from *Petunia, Euonymus, Malus*, or *Fragaria*, preferably obtained from *P. hybrida*, such as PhATF (polypeptide sequence derived from ABG75942.1), *E. alatus*, such as EaCAcT (polypeptide sequence derived from ADF57327.1), *M. domestica* (polypeptide sequence derived from AY517491) or *F. ananassa* (polypeptide sequence derived from AEM43830.1). Furthermore, particularly useful ATF1 enzymes are obtained from *Escherichia*, preferably *E. coli*, such as e.g. EcCAT (polypeptide sequence derived from EDS05563.1).

Thus, in one aspect the present invention is directed to a carotenoid-producing host cell, particularly a fungal host cell, used for biosynthesis of retinoids including vitamin A, said host cell comprising:
  (1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17; and
  (2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39.

According to an aspect of the present invention, the carotenoid-producing host cell comprising (1) stereoselective BCOs as defined herein and (2) trans-acting ATFs, preferably ATF1 enzymes, used in a process for production of retinyl acetate with a percentage of at least 80% present as trans-isoforms in the retinyl acetate mix, said host cell further comprising selective retinol dehydrogenases (RDHs) catalyzing the reduction of retinal into retinol with a total conversion of at least 90% towards production of retinol.

As used herein, the terms "retinal reductase", "retinol dehydrogenase", "enzyme having retinal reducing activity" or "RDH" are used interchangeably herein and refer to enzymes [EC 1.1.1.105] which nearly exclusively (90% or more) are capable of catalyzing the conversion of retinal into retinol, i.e. which are capable of catalyzing the conversion of retinal to retinol with a total conversion of at least about 90%, preferably 92, 95, 97, 98, 99 or even 100% towards retinol formation.

For the purpose of the present invention, any retinal reducing enzyme which results in an increase of at least about 18%, such as e.g. at least about 20, 30, 40, 50, 60, 70, 80, 90, 100% towards formation of retinol can be used in a process as defined herein, such increase being calculated on the retinol formation using endogenous RDHs present in suitable carotenoid-producing host cells, particularly fungal host cells, such as e.g. strains of *Yarrowia* or *Saccharomyces*.

RDHs with activity towards retinol formation, i.e. retinal reduction reaction, as defined herein might be obtained from any source, such as e.g. plants, animals, including humans, algae, fungi, including yeast, or bacteria. Particular useful RDHs are obtained from fungi, in particular Dikarya, including but not limited to fungi selected from Ascomycota, preferably obtained from *Fusarium*, more preferably isolated from *F. fujikuroi*, such as e.g. FfRDH12 (SEQ ID NO:19).

Thus, in a further aspect the present invention is directed to a carotenoid-producing host cell, particularly a fungal host cell, used for biosynthesis of retinoids including vitamin A, said host cell comprising:
  (1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17;
  (2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39; and
  (3) a polypeptide with at least 60%, such as e.g. 65, 70, 75, 80, 85, 90, 95, 97, 98, 99% or up to 100% identity to a polypeptide according to SEQ ID NO:19, encoded by a polynucleotide including a nucleic acid sequence according to SEQ ID NO:20.

According to another aspect of the present invention, the carotenoid-producing host cell according to the present invention is used in a process for production of retinyl acetate with a percentage of at least 65% present as trans-isoforms, said host cell comprising (1) stereoselective or trans-selective BCOs as defined herein, (2) ATFs as defined herein, such as ATF1, with preference for acetylation of trans-retinol, (3) RDHs with about 90% or more activity towards formation of retinol via reduction of retinal, optionally further comprising modifications in the endogenous acyltransferase activity, such as reduced or abolished endogenous activity towards acylating retinol into long chain retinyl esters.

As used herein, the terms "acyltransferase", "retinol acylating enzyme", "enzyme having retinol acylating activity" are used interchangeable herein and refer to enzymes which are capable of catalyzing the conversion of retinol into long chain retinyl esters. Suitable acylating enzymes might be selected from acyl-CoA:diacylglycerol acyltransferase family members [EC 2.3.1], including but not limited to DGATs [EC 2.3.1.20] such as e.g. DGAT1 or DGAT2, ARATs, mdy.

Thus, in one embodiment the present invention is directed to a carotenoid-producing host cell, particularly a fungal host cell, used for biosynthesis of retinoids including vitamin A, said host cell comprising:

(1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17;

(2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39;

(3) a polypeptide with at least 60%, such as e.g. 65, 70, 75, 80, 85, 90, 95, 97, 98, 99% or up to 100% identity to a polypeptide according to SEQ ID NO:19, encoded by a polynucleotide including a nucleic acid sequence according to SEQ ID NO:20; and (4) reduced or abolished activity of a polypeptide having acyltransferase activity catalyzing the acetylation of retinol into long chain retinyl esters, such as DGATs [EC 2.3.1.20].

Modification with regards to acylation activity in a process for production of retinoids using the carotenoid-producing host cell, particularly fungal host cell, as defined herein, means a reduction or abolishment of the endogenous gene(s) encoding acyltransferase activity, such that the activity of endogenous acyltransferases is reduced or abolished, preferably abolished, said host cell being capable or used for production of a retinyl acetate mix comprising at least about 65% in trans-isoform compared to a host cell expressing the respective endogenous acyltransferases prior to the modification of the host cell, i.e. wherein the endogenous acyltransferases are still active. When using said host cell in a vitamin A production process, the percentage of trans-isoforms, such as trans-retinyl acetate, can be increased to about 65% or more, preferably such as 68, 70, 75, 80, 85, 90, 95, 98 or up to 100% based on the total amount of retinyl esters.

Reduction or abolishment of endogenous gene/protein activity, such as retinol acyltransferase activity, might be achieved by, e.g. introducing mutation(s) into the endogenous gene(s) coding for enzymes having said activity, such as acyltransferase activity. The skilled person knows how to genetically manipulate a host cell as defined herein resulting in reduction or abolishment of such activity, e.g. acyltransferase activity. These genetic manipulations include, but are not limited to, e.g. gene replacement, gene amplification, gene disruption, transfection, transformation using plasmids, viruses, or other vectors.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Modifications in order to have the host cell as defined herein produce less or no copies of genes and/or proteins, such as e.g. acylating enzymes as defined herein, i.e. to have less or no acyltransferase activity, may include the use of weak promoters, or the mutation (e.g. insertion, deletion or point mutation) of (parts or) the respective enzymes (as described herein), in particular its regulatory elements. An example of such a genetic manipulation may for instance affect the interaction with DNA that is mediated by the N-terminal region of enzymes as defined herein or interaction with other effector molecules. In particular, modifications leading to reduced or abolished specific enzyme activity may be carried out in functional, such as functional for the catalytic activity, parts of the proteins. Furthermore, reduction or abolishment of enzyme specific activity might be achieved by contacting said enzymes with specific inhibitors or other substances that specifically interact with them. In order to identify such inhibitors, the respective enzymes, such as e.g. the acylating enzymes as defined herein, may be expressed and tested for activity in the presence of compounds suspected to inhibit their activity.

Modifications in order to have the host cell as defined herein produce more copies of genes and/or proteins, such as e.g. stereoselective BCOs, (trans-acting) ATFs and/or RDHs with selectivity towards formation of retinol as defined herein, may include the use of strong promoters, suitable transcriptional- and/or translational enhancers, or the introduction of one or more gene copies into the carotenoid-producing host cell, particularly fungal host cell, leading to increased accumulation of the respective enzymes in a given time. The skilled person knows which techniques to use in dependence of the host cell. The increase or reduction of gene expression can be measured by various methods, such as e.g. Northern, Southern or Western blot technology as known in the art.

The terms "conversion", "oxidation", "reduction", "acylation", "acetylation" in connection with enzymatic catalysis of enzymes as defined herein are art-recognized and refer to actions of the enzymes towards formation/production of retinoids, in particular retinyl acetate.

Preferably, the enzymes used in a process for production of retinoids, in particular retinyl acetate as defined herein, are expressed as heterologous enzymes. They might be integrated on suitable expression vectors or might be integrated in the chromosomal DNA. Such carotenoid-producing host cell, particularly fungal host cell, comprising a heterologous polynucleotide either on an expression vector or integrated into the chromosomal DNA of the host cell is encoding enzymes involved in retinoid production, in particular production of retinyl acetate as described herein, is called a recombinant host cell.

In one particular aspect, the present invention is related to a carotenoid-producing host cell, particularly fungal host cell, carrying one or more (genetic) modifications as defined herein, to be used in a process for production of retinoids, in particular retinyl acetate with at least about 65-90% of the retinyl acetate in trans-isoform and wherein the percentage of acetylated retinol forms, i.e. retinyl esters, such as retinyl acetate, is about at least 10% based on the total amount of retinoids produced by said host cell.

According to another aspect of the present invention, the amount of extracellular retinoids produced with a carotenoid-producing host cell as defined herein can be increased, in particular using a carotenoid-producing host cell which is selected from fungi including yeast, such as e.g. *Yarrowia* or *Saccharomyces*. Thus, a process as described herein leads to at least 80% of retinoids exported outside of the cell, such as e.g. 85, 90, 92, 95, 98, 99 or up to 100% of the retinoids, in particular retinyl acetate with preferably a percentage of about at least 80% in trans-isoform. This is in particular useful with regards to further isolation and purification steps.

Suitable carotenoid-producing host cells used for the process as described herein might be selected from any (micro)organisms, which is suitable for carotenoid/retinoid production and which allows expression of the nucleic acids encoding one of the enzymes as disclosed herein, including functional equivalents or derivatives as described herein. Examples of suitable carotenoid/retinoid-producing host (micro)organisms are bacteria, algae, fungi, including yeasts, plant or animal cells. Preferred bacteria are those of the genera *Escherichia*, such as, for example, *Escherichia coli, Streptomyces, Pantoea (Erwinia), Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis, Paracoccus*, such as, for example, *Paracoccus zeaxanthinifaciens*. Preferred eukaryotic microorganisms, in particular fungi including yeast, are selected from *Saccharomyces*, such as *Saccharomyces cerevisiae, Aspergillus*, such as *Aspergillus niger, Pichia*, such as *Pichia pastoris, Hansenula*, such as *Hansenula polymorpha, Phycomyces*, such as *Phycomyces blakesleanus, Mucor, Rhodotorula, Sporobolomyces, Xanthophyllomyces, Phaffia, Blakeslea*, such as is e.g. *Blakeslea trispora*, or *Yarrowia*, such as *Yarrowia lipolytica*. In particularly preferred is expression in a fungal host cell, such as e.g. *Yarrowia* or *Saccharomyces*, or expression in *Escherichia*, more preferably expression in *Yarrowia lipolytica* or *Saccharomyces cerevisiae*.

With regards to the present invention, it is understood that organisms, such as e.g. microorganisms, fungi, algae, or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

Depending on the host cell, the polynucleotides as defined herein, such as e.g. the polynucleotides encoding BCOs, RDHs, ATFs as defined herein, might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein.

Thus, in one embodiment, the present invention is directed to a carotenoid-producing host cell, particularly fungal host cell, comprising polynucleotides encoding BCOs, ATFs, and/or RDHs as defined herein which are optimized for expression in said host cell, with no impact on growth of expression pattern of the host cell or the enzymes. Particularly, a carotenoid-producing host cell is selected from *Yarrowia*, such as *Yarrowia lipolytica*, comprising optimized polynucleotide sequences selected from the group consisting of SEQ ID NOs: 2, 4, 6, 8, 10, 12, 14, 16, 18, 20, 22, 24, 26, 28, 30, 32, 35, 37 and 39 or sequences with at least 60%, such as e.g. 65, 70, 75, 80, 85, 90, 92, 95, 97, 98, 99% or up to 100% identity thereto.

The present invention is directed to a process for production of a retinyl ester mix comprising retinyl acetate, preferably with a percentage of at least 65% a trans-retinyl acetate, via enzymatic activity of (1) stereospecific BCO as defined herein, comprising contacting beta-carotene with said BCO leading to a retinal mix with a percentage of at least 65%, such as e.g. at least 65-90%, of trans-retinal, and (2) one of the Atf1 enzymes as defined herein, comprising contacting retinol, preferably trans-retinol or a retinol mix with at least 65-90% in trans-isoform, with said Atf1 enzyme. Particularly, the invention is directed to is a process for production of vitamin A, said process comprising (a) introducing a nucleic acid molecule encoding (1) one of the stereoselective BCO enzymes as defined herein and (2) one of the Atf1 enzymes as defined herein into a suitable carotenoid-producing host cell, particularly fungal host cell, as defined herein, (b) enzymatic conversion of beta-carotene into retinal, with at least about 65% of trans-retinal, enzymatic conversion, i.e. acetylation, of retinol, preferably with a percentage of at least 65-90% of trans-retinol, via action of said expressed Atf1 into a mix of trans- and cis-retinyl acetate, and (3) conversion of said retinyl acetate into vitamin A under suitable conditions known to the skilled person.

The terms "sequence identity", "% identity" or "sequence homology" are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when is using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person knows plant-derived enzymes might contain a chloroplast targeting signal which is to be cleaved via specific enzymes, such as e.g. chloroplast processing enzymes (CPEs).

The enzymes as defined herein also encompasses enzymes carrying amino acid substitution(s) which do not alter enzyme activity, i.e. which show the same properties with respect to the wild-type enzyme and catalyze the conversion of beta-carotene to retinal, retinal to retinol, retinol to retinyl acetate, in particular with a total conversion of at least about 65%, such as e.g. at least about 65-90%, towards production of trans-isoform of retinyl acetate. Such mutations are also called "silent mutations", which do not alter the (enzymatic) activity of the enzymes as described herein.

A nucleic acid molecule according to the invention may comprise only a portion or a fragment of the nucleic acid sequence provided by the present invention, for example a fragment which may be used as a probe or primer or a fragment encoding a portion of an enzyme as defined herein. The nucleotide sequence determined from the cloning of the genes encoding the BCOs, ATFs and/or RDHs as defined herein allows for the generation of probes and primers designed for use in identifying and/or cloning other homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequences described herein.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The carotenoid-producing host cell, particularly fungal host cell, as defined herein, which is able to express beta-carotene producing genes, the beta-carotene oxidases as described herein, the retinol acetylating enzymes as defined herein, the retinal reducing enzymes as defined herein, and/or optionally further genes required for biosynthesis of vitamin A, may be cultured in an aqueous medium supplemented with appropriate nutrients under aerobic or anaerobic conditions and as known by the skilled person for the different host cells. Optionally, such cultivation is in the presence of proteins and/or co-factors involved in transfer of electrons, as defined herein. The cultivation/growth of the host cell may be conducted in batch, fed-batch, semi-continuous or continuous mode. Depending on the host cell, preferably, production of retinoids such as e.g. vitamin A and precursors such as retinal, retinol can vary, as it is known to the skilled person. Cultivation and isolation of beta-carotene and retinoid-producing host cells selected from *Yarrowia* is described in e.g. WO2008042338. With regards to production of retinoids in host cells selected from *E. coli*, methods are described in e.g. Jang et al, Microbial Cell Factories, 10:95 (2011). Specific methods for production of beta-carotene and retinoids in yeast host cells, such as e.g. *Saccharomyces cerevisiae*, are disclosed in e.g. WO2014096992.

The present invention is directed to a process for production of retinoids, in particular retinyl acetate with at least about 65% present in trans-isoform and a percentage of at least about 10% in acetylated form, i.e. as retinyl acetate based on the total amount of retinoids produced by the respective host cell, in a carotenoid-producing host cell under conditions as described herein. The produced retinoids, in particular retinyl acetate might be isolated and optionally further purified from the medium and/or host cell.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a system in the presence of a suitable substrate. The skilled person knows how to measure enzyme activity, in particular activity of BCOs, RDHs or ATFs as defined herein. Analytical methods to evaluate the capability of a suitable enzyme as defined herein for retinoid production are known in the art, such as e.g. described in Example 4 of WO2014096992. In brief, titers of products retinoids and carotenoids and the like can be measured by HPLC.

As used herein, a carotenoid-producing host cell, particularly fungal host cell, is a host cell, wherein the respective polypeptides are expressed and active in vivo leading to production of carotenoids, e.g. beta-carotene. The genes and methods to generate carotenoid-producing host cells are known in the art, see e.g. WO2006102342. Depending on the carotenoid to be produced, different genes might be involved.

As used herein, a retinoid-producing host cell, particularly fungal host cell, is a host cell wherein, the respective polypeptides are expressed and active in vivo, leading to production of retinoids, e.g. vitamin A and its precursors, via enzymatic conversion of beta-carotene via retinal, retinol and retinyl acetate. These polypeptides include the BCOs, RDHs and ATFs as defined herein. The genes of the vitamin A pathway and methods to generate retinoid-producing host cells are known in the art. Preferably, the beta-carotene is converted into retinal via action of beta-carotene oxidizing enzymes, the retinal is further converted into retinol via action of RDHs as defined herein, and the retinol, preferably trans-retinol, is converted into retinol acetate via action of acetyltransferase enzymes, such as e.g. ATF1. The retinol acetate might be the is retinoid of choice which is isolated from the host cell.

Retinoids as used herein include beta carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Long chain retinyl esters as used herein define hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid or palmitic acid. Biosynthesis of retinoids is described in e.g. WO2008042338.

Retinal as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

Vitamin A as used herein may be any chemical form of vitamin A found in aqueous solutions, such as for instance undissociated, in its free acid form or dissociated as an anion. The term as used herein includes all precursors or intermediates in the biotechnological vitamin A pathway. It also includes vitamin A acetate.

In particular, the present invention features the present embodiments:

A carotenoid-producing host cell, particularly fungal host cell, comprising: (a) stereoselective beta-carotene oxidizing enzyme (BCO), said host cell producing a retinal mix comprising cis- and trans-retinal, wherein the percentage of trans-retinal in the mix is at least about 65%, preferably 68, 70, 75, 80, 85, 90, 95, 98% or up to 100% produced by said host cell; and (b) an acetyl transferase (ATF) [EC 2.3.1.84], preferably an enzyme with acetyl is transferase 1 (Atf1) activity, said enzyme catalyzing the conversion of retinol, preferably trans-retinol, to a retinyl acetate mix, with a percentage of at least 10% of acetylated retinol, i.e. retinyl acetate, based on the total amount of retinoids produced by said host cell.

A carotenoid-producing host cell, particularly fungal host cell, as above and defined herein, wherein the acetyl transferase [EC 2.3.1.84], preferably an enzyme with acetyl transferase 1 activity, catalyzes the conversion of retinol to a retinyl acetate mix, wherein the mix comprises at least about 65%, preferably 68, 70, 75, 80, 85, 90, 95, 98% or up to 100% retinyl acetate, such as e.g. at least 65-90% retinyl acetate, in trans-isoform.

The carotenoid-producing host cell, particularly fungal host cell, as above and defined herein, further comprising a (preferably heterologous) retinol dehydrogenase (RDH) [EC 1.1.1.105] capable of converting retinal into retinol with a total conversion of at least about 90% towards generation of retinol, preferably RDH obtained from fungi, in particular Dikarya, including but not limited to fungi selected from Ascomycota, more preferably obtained from *Fusarium*, even more preferably isolated from *F. fujikuroi*, such as a polypeptide with at least about 60% identity to FfRDH12 (SEQ ID NO:19).

The carotenoid-producing host cell, particularly fungal host cell, as above and defined herein, furthermore comprising a modification in the endogenous acyltransferase activity, wherein the endogenous acyltransferase activity, preferably [EC 2.3.1] activity, more preferably acyltransferase [EC 2.3.1.20] activity, has been reduced or abolished.

The carotenoid-producing host cell, particularly fungal host cell, as above and defined herein, wherein the BCO is selected from fungi, plants or animal, preferably selected from *Fusarium, Ustilago, Crocus, Drosophila, Danio, Ictalurus, Esox, Latimeria*, more preferably selected from *Fusarium fujikuroi, Ustilago maydis, Crocus sativus, Drosophila melanogaster, Danio rerio, Ictalurus punctatus, Esox Lucius, Latimeria chalumnae* even more preferably selected from a polypeptide with at least about 60% identity to a polypeptide according to SEQ ID NOs:1, 3, 5 or 7 or a polypeptide with at least about 50% identity to a polypeptide sequence according to SEQ ID NOs:9, 11, 13, 15 or 17.

The carotenoid-producing host cell, particularly fungal host cell, as above and defined herein, wherein the acetyl transferase, preferably Atf1, is selected from plants, animals, including humans, algae, fungi, including yeast or bacteria, is preferably selected from *Saccharomyces, Fragaria, Escherichia, Euonymus, Malus, Petunia* or *Lachancea*, more preferably selected from *Saccharomyces bayanus, Fragaria ananassa, Escherichia coli, Euonymus alatus, Malus domestica, Petunia hybrida, Lachancea mirantina* or *Lachancea fermentati*, even more preferably selected from a polypeptide with at least about 60% identity to a polypeptide according to SEQ ID NOs:21, 23, 25, 27, 29, 31, 33, 36, or 38.

The carotenoid-producing host cell, particularly fungal host cell, as above and defined herein, producing a retinyl acetate mix comprising at least about 65%, preferably 68, 70, 75, 80, 85, 90, 95, 98% or up to 100% trans-retinyl acetate isoform, such as at least 65-90% trans-retinyl acetate isoform.

The carotenoid-producing host cell as above and defined herein, wherein the host cell is selected from plants, fungi, algae or microorganisms, preferably selected from fungi including yeast, more preferably from *Saccharomyces, Aspergillus, Pichia, Hansenula, Phycomyces, Mucor, Rhodotorula, Sporobolomyces, Xanthophyllomyces, Phaffia, Blakeslea or Yarrowia, even more preferably from Yarrowia lipolytica or Saccharomyces cerevisiae.

The carotenoid-producing host cell as above and defined herein, wherein the host cell is selected from plants, fungi, algae or microorganisms, preferably selected from Escherichia, Streptomyces, Pantoea, Bacillus, Flavobacterium, Synechococcus, Lactobacillus, Corynebacterium, Micrococcus, Mixococcus, Brevibacteriurn, Bradyrhizobium, Gordonia, Dietzia, Muricauda, Sphingomonas, Synochocystis or Paracoccus.

The carotenoid-producing host cell, particularly fungal host cell, as above and defined herein used in a process for conversion of beta-carotene into vitamin A.

A process for production of trans-retinyl acetate comprising cultivation of the carotenoid-producing host cell, particularly fungal host cell, as above and defined herein in an aqueous medium under suitable culture conditions and isolating and optionally further purifying said trans-retinyl acetate from the medium and/or host cell.

A process for production of vitamin A comprising the steps of:
(a) introducing a nucleic acid molecule encoding stereoselective BCO as defined herein, acetyl transferase [EC 2.3.1.84] as defined herein, optionally retinol dehydrogenase [EC 1.1.1.105] as defined herein, into a suitable carotene-producing host cell, particularly fungal host cell;
(b) optionally reducing or abolishing the endogenous acyltransferase activity [EC 2.3.1] as defined herein of the cell of (a),
(c) enzymatic conversion of beta-carotene into retinyl acetate mix comprising a ratio of trans to cis-retinyl acetate of 4; and
(d) conversion of retinyl acetate into vitamin A under suitable culture conditions.

A process for production of vitamin A comprising the steps of:
(a) introducing a nucleic acid molecule encoding stereoselective BCO, acetyl transferase [EC 2.3.1.84], optionally retinol dehydrogenase [EC 1.1.1.105], into a suitable host cell;
(b) optionally reducing or abolishing the endogenous acyltransferase activity [EC 2.3.1] of the cell of (a),
(c) enzymatic conversion of beta-carotene into retinoids comprising at least a percentage of 10% retinyl acetate, said retinyl acetates comprising at least a percentage of 65% in trans isoform based on the total amount of produced retinoids; and
(d) conversion of retinyl acetate into vitamin A under suitable culture conditions.

The following examples are illustrative only and are not intended to limit the scope of the invention in any way. The contents of all references, patent applications, patents, and published patent applications, cited throughout this application are hereby incorporated by reference, in particular WO2006102342, WO2008042338 or WO2014096992.

EXAMPLES

Example 1: General Methods, Strains, and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake plate assay. Typically, 800 µl of 0.075% Yeast extract, 0.25% peptone (0.25×YP) is inoculated with 10 µl of freshly grown Yarrowia and overlaid with 800 µl of mineral oil (Drakeol 5, Penreco Personal Care Products, Karns City, PA, USA) carbon source 5% corn oil in mineral oil and/or 5% in glucose in aqueous phase. Transformants were grown in 24 well plates (Microplate Devices 24 Deep is Well Plates Whatman 7701-5102), covered with mat seal (Analytical Sales and Services Inc. Plate Mats 24010CM), sterile sealed with Qiagen Airpore Tape Sheets (19571) and shaken in Infors multi plate shaker (Multitron), 30° C., 800 RPM in YPD media with for 4 days. The mineral oil fraction was removed from the shake plate wells and analyzed by HPLC on a normal phase column, with a photo-diode array detector. This method is used in Examples 2, 3, 4.

DNA transformation. Strains are transformed by overnight growth on YPD plate media 50 µl of cells is scraped from a plate and transformed by incubation in 500 µl with 1 µg transforming DNA, typically linear DNA for integrative transformation, 40% PEG 3550MW, 100 mM lithium acetate, 50 mM Dithiothreitol, 5 mM Tris-Cl pH 8.0, 0.5 mM EDTA for 60 minutes at 40° C. and plated directly to selective media or in the case of dominant antibiotic marker selection the cells are out grown on YPD liquid media for 4 hours at 30° C. before plating on the selective media.

DNA molecular biology. Genes were synthesized with NheI and MluI ends in pUC57 vector (GenScript, Piscataway, NJ). Typically, the genes were subcloned to the MB5082 'URA3', MB6157 HygR, and MB8327 NatR vectors for marker selection in Yarrowia lipolytica transformations, as in WO2016172282. For clean gene insertion by random nonhomologous end joining of the gene and marker HindIII/XbaI (MB5082) or PvuII (MB6157 and MB8327), respectively purified by gel electrophoresis and Qiagen gel purification column. MB5082 'URA3' marker could be reused due to gratuitous repeated flanking sequences that enable selection of circular excisants of the URA3 cassette on FOA. The NatR and HygR markers can be removed by transient expression of Cre recombinase that results in excisants due to the flanking Lox sites.

Plasmid list. Plasmid, strains, nucleotide and amino acid sequences to be used are listed in Table 1, 2 and the sequence listing. Nucleotide sequence ID NOs:2, 4, 6, 8, 10, 12, 14, 16, 18, 20, 22, 24, 26, 28, 30, 32, 35, 37, and 39 are codon optimized for expression in Yarrowia.

TABLE 1 list of plasmids used for construction of the strains carrying the heterologous BCO, RDH and ATF1-genes. The sequence ID NOs refer to the inserts. For more details, see text.

| MB plasmid | Backbone MB | Insert | SEQ ID NO: (aa/nt) |
|---|---|---|---|
| 8457 | 5082 | UmCCO1 | 1/2 |
| 8456 | 5082 | FfCarX | 3/4 |
| 6703 | 5082 | CsZCO | 5/6 |
| 6702 | 5082 | DmNinaB | 7/8 |
| 9068 | 5082 | DrBCO | 9/10 |
| 9279 | 5082 | DrBCO-TPI | 11/12 |
| 9123 | 5082 | IpBCO | 13/14 |
| 9121 | 5082 | ElBCO | 15/16 |
| 9126 | 5082 | LcBCO | 17/18 |
| 8200 | 5082 | FfRDH12 | 19/20 |

TABLE 1-continued list of plasmids used for construction of the strains carrying the heterologous BCO, RDH and ATF1-genes. The sequence ID NOs refer to the inserts. For more details, see text.

| MB plasmid | Backbone MB | Insert | SEQ ID NO: (aa/nt) |
|---|---|---|---|
| 8064 | 5082 | SbATF1 | 21/22 |
| 8509 | 6157 | FaATF | 23/24 |
| 8510 | 6157 | EcCAT | 25/26 |
| 8511 | 6157 | EaCAcT | 27/28 |
| 8512 | 6157 | MdATF | 29/30 |
| 8513 | 6157 | PhATF | 31/32 |
| 8849 | 5082 | LmATF1 | 33/35 |
| 8610 | 5082 | LfATF1 | 36/37 |
| 8806 | 5082 | LffATF1 | 38/39 |

TABLE 2 list of Yarrowia strains used for production of retinoids carrying the heterologous BCO, RDH and ATF1-genes. For more details, see text.

| ML strain | Description | First described in |
|---|---|---|
| 7788 | Carotene strain | WO2016172282 |
| 15710 | ML7788 transformed with MB7311 -Mucor CarG | WO2016172282 |
| 17544 | ML15710 cured of URA3 by FOA and HygR by Cre/lox | here |
| 17767 | ML17544 transformed with MB6072 DmBCO-URA3 and MB6732 SbATF1-HygR and cured of markers | here |
| 17968 | ML17544 transformed with MB8457 UmCCO1-URA3 and cured of markers | here |
| 17978 | ML17968 transformed with MB8200 FfRDH-URA3 and cured of markers | here |

Normal phase retinol method. A Waters 1525 binary pump attached to a Waters 717 auto sampler were used to inject samples. A Phenomenex Luna 3p Silica (2), 150×4.6 mm with a security silica guard column kit was used to resolve retinoids. The mobile phase consists of either, 1000 mL hexane, 30 mL isopropanol, and 0.1 mL acetic acid for astaxanthin related compounds, or 1000 mL hexane, 60 mL isopropanol, and 0.1 mL acetic acid for zeaxanthin related compounds. The flow rate for each is 0.6 mL per minute. Column temperature is ambient. The injection volume is 20 µL. The detector is a photodiode array detector collecting from 210 to 600 nm. Analytes were detected according to Table 3.

TABLE 3 list of analytes using normal phase retinol method. The addition of all added intermediates gives the amount of total retinoids. For more details, see text.

| Intermediates | Retention time [min] | Lambda max [nm] |
|---|---|---|
| 11-cis-dihydro-retinol | 7.1 | 293 |
| 11-cis-retinal | 4 | 364 |
| 11-cis-retinol | 8.6 | 318 |
| 13-cis-retinal | 4.1 | 364 |
| dihydro-retinol | 9.2 | 292 |
| retinyl-acetate | 3.5 | 326 |
| retinyl-ester | 3 | 325 |
| trans-retinal | 4.7 | 376 |
| trans-retinol | 10.5 | 325 |

Sample preparation. Samples were prepared by various methods depending on the conditions. For whole broth or washed broth samples the broth was placed in a Precellys® tube weighed and mobile phase was added, the samples were processed in a Precellys® homogenizer (Bertin Corp, Rockville, MD, USA) on the highest setting 3× according to the manufactures directions. In the washed broth the samples were spun in a 1.7 ml tube in a microfuge at 10000 rpm for 1 minute, the broth decanted, 1 ml water added mixed pelleted and decanted and brought up to the original volume the mixture was pelleted again and brought up in appropriate amount of mobile phase and processed by Precellys® bead beating. For analysis of mineral oil fraction, the sample was spun at 4000 RPM for 10 minutes and the oil was decanted off the top by positive displacement pipet (Eppendorf, Hauppauge, NY, USA) and diluted into mobile phase mixed by vortexing and measured for retinoid concentration by HPLC analysis.

Fermentation conditions. Fermentations were identical to the previously described conditions using preferably a silicone oil or a mineral oil overlay and stirred tank that was preferably glucose or corn oil fed in a bench top reactor with 0.5 L to 5 L total volume (see WO2016172282). Generally, the same results were observed with a fed batch stirred tank reactor with an increased productivity demonstrating the utility of the system for the production of retinoids. Preferably, fermentations were batched with 5% glucose and 20% silicone oil was added after dissolved oxygen plummeted and feed was resumed to achieve 20% dissolved oxygen throughout the feeding program. Alternatively, corn oil was used as a feed and mineral oil was used as a second phase to collect the aliphatic retinoids.

Example 2: Conversion of Beta-Carotene to Retinal in *Yarrowia lipolytica*

For expression of heterologous BCOs, a beta carotene strain ML17544 was transformed with purified linear DNA fragment by HindII and XbaI mediated restriction endonucleotide cleavage and gel purification of beta carotene oxidase (BCO) containing codon optimized fragments linked to a URA3 nutritional marker. Transforming DNA were derived from MB6702 *Drosophila* NinaB BCO gene, MB6703 *Crocus* BCO gene, MB8456 *Fusarium* BCO gene, and MB8457 *Ustilago* BCO gene and MB6098 Dario BCO gene, whereby the codon-optimized sequences (SEQ ID NOs:2, 4, 6, 8, 10, 12) had been used. The genes were then grown screening 6-8 isolates in a shake plate analysis, and isolates that is performed well were run in a fed batch stirred tank reaction for 8-10 days. Detection of cis- and trans-retinal was made by HPLC using standard parameters as described in WO2014096992, but calibrated with purified standards for the retinoid analytes. The amount of trans-retinal in the retinal mix could be increased to 90% (using the *Crocus* BCO), 95% (using the *Fusarium* BCO), 98%

(using the *Ustilago* BCO) and 98% (using Dario BCO), respectively. A comparison with the BCO from *Drosophila melanogaster* (SEQ ID NO:7) resulted in 61% of trans-retinal based on the total amount of retinal (see Table 4).

TABLE 4

Retinal production in *Yarrowia* as enhanced by action of heterologous BCOs. "% trans" means percentage of trans-retinal in the mix of retinoids. For more details, see text.

| Organism | BCO gene | % trans- | % retinoids/DCW | ML strain | MB plasmid |
|---|---|---|---|---|---|
| Drosophila | DmNinB | 61 | 14 | 17544 | 6702 |
| Ustilago | UmCCO1 | 98 | 8 | 17544 | 8457 |
| Fusarium | FfCarX | 95 | 5 | 17544 | 8456 |
| Crocus | ZsZCO | 90 | 0.01 | 17544 | 6703 |
| Dario | DrBCO | 98 | 6 | 17544 | 9068 |
| Dario | DrBCO-TPI | 98 | 6 | 17544 | 9279 |
| Ictalurus | IpBCO | 98 | 5 | 17544 | 9123 |
| Esox | ElBCO | 98 | 3 | 17544 | 9121 |
| Latimeria | LcBCO | 98 | 2 | 17544 | 9126 |

Example 3: Conversion of Retinal to Retinol in *Yarrowia lipolytica*

For expression of heterologous RDHs, the beta carotene strain ML17767 was transformed with purified HinDIII/XbaI fragments derived from plasmids containing retinol dehydrogenase (RDH) gene fragments linker to a URA3 promoter. Six to eight isolates were screened for a decrease in the retinol:retinal ratio in a shake plate assay and successful isolates were run in a fed batch stirred tank reactor for eight days which showed an order of magnitude increase in the productivity of the process which indicates a utility in large scale production. The best results were obtained with the *Fusarium* RDH12 homolog with only 2% or residual retinal maintained after 8 days of shake-flask incubation as described above. The isolate derived from the *Fusarium* sequence demonstrated an increased reduction of retinol.

Example 4: Conversion of Retinol to Retinyl Acetate in *Yarrowia lipolytica*

For expression of heterologous ATF1, the trans retinol producing strain ML17968 was transformed with purified PvuII gene fragments containing acetyltransferase gene fragments linked to a Hygromycin resistance marker (HygR) for selection rich media (YPD) containing 100 ug/ml hygromycin. Prior to plating the cultures were outgrown in YPD for four hours to synthesize the antibiotic resistance genes. Isolates were screened for acylation in shake plate assays and successful isolates were screened in fed batch stirred tank reactor which showed an order of magnitude increased productivity indicating utility in the production of retinoids. The data from the analysis are shown in Table 5).

TABLE 5

Trans retinoid production in *Yarrowia* as enhanced by action of heterologous ATF1 enzymes. "% acetylation" means percentage of trans-retinyl acetate in the mix of retinoids. For more details, see text.

| Organism | ATF1 gene | % acetylation- | ML strain | MB plasmid |
|---|---|---|---|---|
| S. bayanus | SbATF1 | 10.3 | 17968 | 6832 |
| P. hybrida | PhATF | 2.1 | 17968 | 8513 |
| E. alatus | EaCAcT | 0.45 | 17968 | 8511 |
| E. coli | EcCAT | 0.35 | 17968 | 8510 |
| L. fermentata | LfATF1 | 9.6 | 18523 | 8610 |
| L. fermentata | LffATF1 | 11.7 | 18523 | 8806 |
| L. mirantina | LmATF1 | 40.4 | 18523 | 8849 |

Example 5: ATF1 Activity Assay

For expression of heterologous ATF1, the trans retinol producing strain ML17968 was transformed with purified PvuII gene fragments containing acetyltransferase gene fragments linked to a Hygromycin resistance marker (HygR) for selection rich media (YPD) containing 100 ug/ml hygromycin. Prior to plating the cultures were outgrown in YPD for four hours to synthesize the antibiotic resistance genes. Isolates were screened for acylation in shake plate assays, specifically using 10% glucose as a carbon source in 0.25× YP with silicone oil as an overlay and successful isolates were further screened in fed batch stirred tank reactor with glucose feed and silicone oil overlay, which showed an order of magnitude increased productivity indicating utility in the production of retinoids. The data from the analysis are shown in Table 5.

Example 6: Conversion of Beta-Carotene to Retinyl Acetate in *Saccharomyces cerevisiae*

Typically, a beta carotene strain is transformed with heterologous genes encoding for enzymes such as geranylgeranyl synthase, phytoene synthase, lycopene synthase, lycopene cyclase constructed that is producing beta carotene according to standard methods as known in the art (such as e.g. as described in US20160130628 or WO2009126890). Further, when transformed with beta carotene oxidase genes retinal can be produced. Further, when transformed with retinol dehydrogenase, then retinol can be produced. The retinol can be acetylated by transformation with genes encoding alcohol acetyl transferases. Optionally, the endogenous retinol acylating genes can be deleted. Further, the enzymes can be selected to produce and acylate the trans form of retinol to yield all trans retinyl acetate, and long chain esters of trans retinol, respectively. With this approach, similar results regarding specificity for trans-isoform or productivity towards retinyl acetate are obtained.

The invention claimed is:

1. A process for production of vitamin A comprising cultivating a retinoid-producing fungal host cell in an aqueous medium under suitable culture conditions, wherein
   (a) the host cell expresses
      (i) a heterologous beta-carotene oxidizing enzyme (BCO) capable of catalyzing the conversion of beta-carotene into a retinal mix comprising cis- and trans-retinal,
      (ii) a heterologous retinol dehydrogenase (RDH) enzyme [EC 1.1.1.105] capable of converting retinal into retinol, and
      (iii) a heterologous acetyl transferase 1 enzyme (ATF1) [EC 2.3.1.84] capable of catalysing the conversion of trans-retinol to a retinyl acetate, and
   (b) the host cell is capable of
      (i) producing a retinal mix comprising cis- and trans-retinal,
      (ii) converting the retinal mix into retinol with a total conversion of at least 90% towards generation of retinol, and
      (iii) converting the retinol into retinyl acetate, wherein at least 40% of the total amount of retinoids produced by said host cell is retinyl acetate.

2. The process according to claim 1, wherein the heterologous ATF1 is capable of catalysing the conversion of trans-retinol into trans-retinyl acetate.

3. The process according to claim 1, wherein the heterologous RDH is a fungal RDH [EC 1.1.1.105].

4. The process according to claim 1, wherein the host cell further comprises a modification to reduce or abolish the activity of one or more endogenous acyltransferase(s) [EC 2.3.1] catalyzing the acylation of retinol into long chain retinyl esters.

5. The process according to claim 1, wherein the heterologous BCO is a fungal, plant or animal BCO.

6. The process according to claim 1, wherein the heterologous ATF1 is a fungal, bacterial, plant or animal ATF1.

7. The process according to claim 1, wherein the host cell produces a retinyl acetate mix comprising at least 65% trans-retinyl acetate isoform.

8. The process according to claim 1, wherein the fungal host cell is a yeast cell.

9. The process according to claim 1 further comprising isolating said vitamin A.

10. The process according to claim 7 further comprising isolating said vitamin A.

11. The process according to claim 1, wherein the heterologous ATF1 comprises an amino acid sequence with at least 90% identity to SEQ ID NO: 33.

12. The process according to claim 11, wherein the heterologous BCO and RDH comprises an amino acid sequence with at least 90% identity to SEQ ID NO: 9 and 19, respectively.

13. The process according to claim 11, wherein the fungal host cell is a yeast cell.

14. The process according to claim 11, wherein the fungal host cell is a *Saccharomyces* or *Yarrowia* cell.

15. The process according to claim 11, wherein the fungal host cell is a *Yarrowia lipolytica* or *Saccharomyces cerevisiae* cell.

16. The process according to claim 11, wherein the fungal host cell further comprises a mutation in a gene encoding an endogenous acyltransferase enzyme that is capable of catalyzing the conversion of retinol into a long chain retinyl ester.

17. The process according to claim 12, wherein the fungal host cell is a yeast cell.

18. The process according to claim 12, wherein the fungal host cell is a *Saccharomyces* or *Yarrowia* cell.

19. The process according to claim 12, wherein the fungal host cell is a *Yarrowia lipolytica* or *Saccharomyces cerevisiae* cell.

20. The process according to claim 12, wherein the fungal host cell further comprises a mutation in a gene encoding an endogenous acyltransferase enzyme that is capable of catalyzing the conversion of retinol into a long chain retinyl ester.

* * * * *